(12) United States Patent
Powers et al.

(10) Patent No.: US 8,076,376 B2
(45) Date of Patent: Dec. 13, 2011

(54) ANILINE SULFONAMIDE DERIVATIVES AND THEIR USES

(76) Inventors: Jay P. Powers, Pacifica, CA (US); Xiao He, Foster City, CA (US); Dustin McMinn, Pacifica, CA (US); Yosup Rew, Foster City, CA (US); Daqing Sun, Forest City, CA (US)

(*) Notice: Subject to any disclaimer, the term of this patent is extended or adjusted under 35 U.S.C. 154(b) by 1543 days.

(21) Appl. No.: 11/490,143

(22) Filed: Jul. 21, 2006

(65) Prior Publication Data

US 2007/0021502 A1    Jan. 25, 2007

Related U.S. Application Data

(60) Provisional application No. 60/701,476, filed on Jul. 22, 2005.

(51) Int. Cl.
*A61K 31/18* (2006.01)
*C07C 311/37* (2006.01)
(52) U.S. Cl. .......................................... 514/604; 564/92
(58) Field of Classification Search .................. 514/604; 564/92
See application file for complete search history.

(56) References Cited

U.S. PATENT DOCUMENTS

| | | |
|---|---|---|
| 2002/0048572 A1 | 4/2002 | Shan et al. |
| 2002/0119521 A1 | 8/2002 | Palli et al. |
| 2003/0073614 A1 | 4/2003 | Schulman et al. |
| 2003/0162758 A1 | 8/2003 | Schwartz et al. |
| 2003/0229062 A1 | 12/2003 | Schwartz et al. |
| 2004/0018560 A1 | 1/2004 | Bledsoe et al. |

FOREIGN PATENT DOCUMENTS

| | | |
|---|---|---|
| CA | 2377999 AA | 1/2001 |
| CA | 2438133 AA | 8/2002 |
| JP | 2003267969 A2 | 9/2003 |
| JP | 2004500332 T2 | 1/2004 |
| JP | 2004524027 T2 | 8/2004 |
| JP | 2004533216 | 11/2004 |
| WO | WO0054759 A2 | 9/2000 |
| WO | WO 01/03705 A1 | 1/2001 |
| WO | WO01/70816 A2 | 9/2001 |
| WO | WO 01/82917 A2 | 11/2001 |
| WO | WO 02/066612 A2 | 8/2002 |
| WO | WO 02/066615 A2 | 8/2002 |
| WO | WO03/049685 A2 | 6/2003 |
| WO | WO03063576 A2 | 8/2003 |
| WO | WO03082198 A2 | 10/2003 |
| WO | WO2004058175 A2 | 7/2004 |
| WO | WO2004058819 A2 | 7/2004 |
| WO | WO 2004/065351 A1 | 8/2004 |
| WO | WO 2004/089896 A1 | 10/2004 |
| WO | WO2004098506 A2 | 11/2004 |
| WO | WO2004101776 A2 | 11/2004 |
| WO | WO2004104224 A2 | 12/2004 |

OTHER PUBLICATIONS

International Search Report for PCT Application No. PCT/US2006/028059 mailed on Nov. 13, 2006.

Li, Leping, et al., Discovery and Optimization of a novel series of liver X receptor-agonists, Bioorganic & Medicinal Chemistry Letters 16 (2006) 1638-1642.

Stein, et al., LXR Activation and Cholesterol Efflux from a Lipoprotein Depot in vivo, Biochimica et Biophysica Acta (2004), vol. 1686 (1-2), pp. 24-29.

Fukuchi, et al., Antiproliferative Effect of Liver X Receptor Agonists on LNCaP Human Prostate Cancer Cells, Cancer Research (2004), vol. 64(21), pp. 7686-7689.

Jakel, et al., The Liver X Receptor Ligand T0901317 Down-regulates APOA5 Gene Expression through Activation of SREBP-1c, Journal of Biological Chemistry (2004), vol. 279(44), pp. 45462-45469.

Quinet, et al., Gene-selective Modulation by a Synthetic Oxysterol Ligand of the Liver X Receptor, Journal of Lipid Research, (2004), vol. 45(10), pp. 1929-1942.

Houck, et al., T0901317 is a Dual LXR/FXR Agonist, Molcular Genetics and Metabolism, (2004), vol. 83(1/2), pp. 184-187.

Miao, et al., Raising HDL Cholesterol Without Inducing Hepatic Steatosis and Hypertriglyceridemia by a Selective LXR Modulator, Journal of Lipid Research, (2004), vol. 45(8), pp. 1410-1417.

Liang, et al., Liver X Receptors (LXRs) Regulate Apolipoprotein AIV-Implications of the Antiatherosclerotic Effect of LXR Agonists, Molecular Endocrinology, (2004), vol. 18(8), pp. 2000-2010.

Schmuth, et al., The Effect of LXR Activators on AP-1 Proteins in Keratinocytes, Journal of Investigative Dermatology, (2004), vol. 123(1), pp. 41-48.

Beyer, et al., Coadministration of a Liver X Receptor Agonist and a Peroxisome Proliferator Activator Receptor-α Agonist in Mice: Effects of Nuclear Receptor Interplay on High-Denisty Lipoprotein and Triglyceride Metabolism in Vivo, Journal of Pharmacology and Experimental Therapeutics, (2004), vol. 309(3), pp. 861-868.

Toresson, et al., Purification of Functional Full-Length Liver X Receptor β Produced in *Escherichia coli*, Protein Expression and Purification, (2004), vol. 35(2), pp. 190-198.

Seo, et al., Activated Liver X Receptors Stimulate Adipocyte Differentiation Through Induction of Peroxisome Proliferator-Activated Receptor γ Expression, Molecular and Cellular Biology, (2004), vol. 24(8), pp. 3430-3444.

Masson, et al., Cholesteryl Ester Transfer Protein Modulates the Effect of Liver X Receptor Agonists on Cholesterol Transport and Excretion in the Mouse, Journal of Lipid Research, (2004), vol. 45(3), pp. 543-550.

(Continued)

*Primary Examiner* — Peter O Sullivan
(74) *Attorney, Agent, or Firm* — Elsa D. Lemoine

(57) ABSTRACT

Aniline sulfonamide derivatives according to formula I have therapeutic utility, particularly in the treatment of diabetes, obesity and related conditions and disorders:

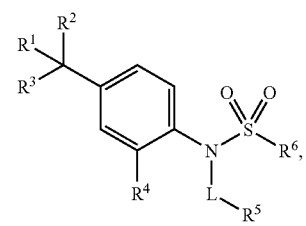

where $R^1$, $R^2$, $R^3$, $R^4$, $R^5$, $R^6$, and L are set forth in the description.

23 Claims, No Drawings

OTHER PUBLICATIONS

Liang, et al., A Liver X Receptor and Retinoid X Receptor Heterodimer Mediates Apolipoprotein E Expression, Secretion and Cholesterol Homeostasis in Astrocytes, Journal of Neurochemistry, (2004), vol. 88(3), pp. 623-634.

Chisholm, et al., The LXr Ligand T0901317 Induces Severe Lipogenesis in the db/db Diabetic Mouse, Journal of Lipid Research, (2003), vol. 44(11), pp. 2039-2048.

Hoerer, et al., Crystal Structure of the Human Liver X Receptor β Ligand-Binding Domain in Complex with a Synthetic Agonist, Journal of Molecular Biology, (2003), vol. 334(5), pp. 853-861.

Rowe, et al., Enhanced Synthesis of the Oxysterol 24(S), 25-Epoxycholesterol in Macrophages by Inhibitors of 2,3-Oxidosqualene: Lanosterol Cyclase, Circulation Research, (2003), vol. 93(8), pp. 717-725.

Faernegardh, et al., The Three-Dimensional Structure of the Liver X Receptor β Reveals a Flexible Ligand-Binding Pocket That Can Accommodate Fundamentally Different Ligands, Journal of Biological Chemistry, (2003), vol. 278(40), pp. 38821-38828.

Svensson, et al., Crystal Structure of the Heterodimeric Complex of LXRα and Rxrβ Ligand-Binding Domains in a Fully Agonistic Conformation, EMBO Journal, (2003), vol. 22(18), pp. 4625-4633.

Kaneko, et al., Induction of Intestinal ATP-Binding Cassette Transporters by a Phytosterol-Derived Liver X Receptor Agonist, Journal of Biological Chemistry, (2003), vol. 278(38), pp. 36091-36098.

Miyazaki, et al., Identification and Characterization of Murine SCD4, a Novel Heart-Specific Stearoyl-CoA Desaturase Isoform Regulated by Leptin and Dietary Factors, Journal of Biological Chemistry, (2003), vol. 278(36), pp. 33904-33911.

Wang, et al., Molecular Determinants of LXRα Agonism, Journal of Molecular Graphics & Modelling, (2003), vol. 22(2), pp. 173-181.

Williams, et al., X-ray Crystal Structure of the Liver X Receptor β Ligand Binding Domain: Regulation by a Histidine-Tryptophan Switch, Journal of Biological Chemistry, (2003), vol. 278(29), pp. 27138-27143.

Yoshikawa, et al., Cross-Talk Between Peroxisome Proliferator-Activated Receptor (PPAR) α and Liver X Receptor (LXR) in Nutritional Regulation of Fatty Acid Metabolism. I. PPARs Suppress Sterol Regulatory Element Binding Protein-1c Promoter Through Inhibition of LXR Signaling, Molecular Endocrinology, (2003), vol. 17(7), pp. 1240-1254.

Perez, et al., Expression of Nuclear Receptors and Apo E Secretion During the Differentiation of Monocytic THP-1 Cells Into Macrophages, Cell Biology and Toxicology, (2003), vol. 19(2), pp. 95-105.

Goodwin, et al., Differential Regulation of Rat and Human CYP7A1 by the Nuclear Oxysterol Receptor Liver X Receptor-α, Molecular Endocrinology, (2003), vol. 17(3), pp. 386-394.

Juvet, et al., On the Role of Liver X Receptors in Lipid Accumulation in Adipocytes, Molecular Endocrinology, (2003), vol. 17(2), pp. 172-182.

Terasaka, et al., T-0901317, a Synthetic Liver X Receptor Ligand, Inhibits Development of Atherosclerosis in LDL Receptor-Deficient Mice, FEBS Letters, (2003), vol. 536(1-3), pp. 6-11.

Kaplan, et al., Regulation of the Angiopoietin-Like Protein 3 Gene by LXR, Journal of Lipid Research, (2003), vol. 44(1), pp. 136-143.

Cao, et al., Antidiabetic Action of a Liver X Receptor Agonist Mediated by Inhibition of Hepatic Gluconeogenesis, Journal of Biological Chemistry, (2003), vol. 278(2), pp. 1131-1136.

Brendel, et al., The Small Heterodimer Partner Interacts With the Liver X Receptor α and Represses its Transcriptional Activity, Molecular Endocrinology, (2002), vol. 16(9), pp. 2065-2076.

Stulnig, et al., Liver X Receptors Downregulate 11β-hydroxysteroid Dehydrogenase Type 1 Expression and Activity, Diabetes, (2002), vol. 51(8), pp. 2426-2433.

Murthy, et al., LXR/RXR Activation Enhances Basolateral Efflux of Cholesterol in CaCo-2 Cells, Journal of Lipid Research, (2002), vol. 43(7), pp. 1054-1064.

Collins, et al., Identification of a Nonsteroidal Liver X Receptor Agonist Through Parallel Array Synthesis of Tertiary Amines, Journal of Medicinal Chemistry, (2002), vol. 45(10), pp. 1963-1966.

Song, et al., Hypolipidemic Effects of Selective Liver X Receptor Alpha Agonists, Steroids, (2001), vol. 66(9), pp. 673-681.

Schultz, et al., Role of LXRs in Control of Lipogenesis, Genes & Development, (2000), vol. 14(22), pp. 2831-2838.

ANILINE SULFONAMIDE DERIVATIVES AND THEIR USES

BACKGROUND OF THE INVENTION

This invention is generally directed to novel compounds, compositions, and the use of either in methods for modulating hydroxysteroid dehydrogenases, such as 11β-HSD1, and for treating or preventing diseases associated with the modulation of hydroxysteroid dehydrogenases, such as diabetes and obesity. The methods comprise the administration, to a patient in need thereof, of a therapeutically effective amount of an aniline sulfonamide derivative. Novel aniline sulfonamide derivatives or pharmaceutically acceptable salts, solvates, stereoisomers, or prodrugs thereof are presented herein.

Hydroxysteroid dehydrogenases (HSDs) regulate the occupancy and activation of steroid hormone receptors by converting steroid hormones into their inactive metabolites. For a recent review, see Nobel et al., *Eur. J. Biochem.* 2001, 268:4113-4125.

There exist numerous classes of HSDs. The 11-beta-hydroxysteroid dehydrogenases (11β-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1(11β-HSD1) is expressed in liver, adipose tissue, brain, lung and other glucocorticoid tissue and is a potential target for therapy directed at numerous disorders that may be ameliorated by reduction of glucocorticoid action, such as diabetes, obesity and age-related cognitive dysfunction. Seckl, et al., *Endocrinology,* 2001, 142:1371-1376.

It is well known that glucocorticoids play a central role in the development of diabetes and that glucocorticoids enable the effect of glucagon on the liver. Long et al., *J. Exp. Med.* 1936, 63: 465-490; and Houssay, *Endocrinology* 1942, 30: 884-892. In addition, it has been well substantiated that 11β-HSD1 plays an important role in the regulation of local glucocorticoid effect and of glucose production in the liver. Jamieson et al., *J. Endocrinol.* 2000, 165:685-692. In Walker, et al., *J. Clin. Endocrinol. Metab.* 1995, 80:3155-3159, it was reported that the administration of the non-specific 11β-HSD1 inhibitor carbenoxolone resulted in improved hepatic insulin sensitivity in humans.

Furthermore, the hypothesized mechanism of action of HSDs in the treatment of diabetes has been supported by various experiments conducted in mice and rats. These studies showed that the mRNA levels and activities of two key enzymes in hepatic glucose production, phosphoenolpyruvate carboxykinase (PEPCK), and glucose-6-phosphatase (G6Pase) were reduced upon administration of HSD inhibitors. In addition, blood glucose levels and hepatic glucose production were shown to be reduced in 11β-HSD1 knockout mice. Additional data gathered using this murine knockout model also confirm that inhibition of 11β-HSD1 will not cause hypoglycemia, since the basal levels of PEPCK and G6Pase are regulated independently of glucocorticoids. Kotelevtsev et al., *Proc. Natl. Acad. Sci. USA* 1997, 94: 14924-14929.

HSDs are also believed to play a role in obesity. Obesity is an important factor in Syndrome X as well as type II (non-insulin dependent) diabetes, and omental fat appears to be of central importance in the development of both of these diseases, as abdominal obesity has been linked with glucose intolerance, hyperinsulinemia, hypertriglyceridemia, and other factors of Syndrome X (e.g., raised blood pressure, decreased levels of HDL and increased levels of VLDL). Montague et al., *Diabetes* 2000, 49:883-888, 2000. It has also been reported that inhibition of the 11β-HSDs in pre-adipocytes (stromal cells) resulted in a decreased rate of differentiation into adipocytes. This is predicted to result in diminished expansion (possibly reduction) of the omental fat depot, which may lead to reduced central obesity. Bujalska et al., *Lancet* 1997, 349:1210-1213.

Inhibition of 11β-HSD1 in mature adipocytes is expected to attenuate secretion of the plasminogen activator inhibitor 1 (PAI-1), which is an independent cardiovascular risk factor, as reported in Halleux et al., *J. Clin. Endocrinol. Metab.* 1999, 84:4097-4105. In addition, a correlation has been shown to exist between between glucocorticoid activity and certain cardiovascular risk factors. This suggests that a reduction of the glucocorticoid effects would be beneficial in the treatment or prevention of certain cardiovascular diseases. Walker et al., *Hypertension* 1998, 31:891-895; and Fraser et al., *Hypertension* 1999, 33:1364-1368.

HSDs have also been implicated in the process of appetite control and therefore are believed to play an additional role in weight-related disorders. It is known that adrenalectomy attenuates the effect of fasting to increase both food intake and hypothalamic neuropeptide Y expression. This suggests that glucocorticoids play a role in promoting food intake and that inhibition of 11β-HSD1 in the brain may increase satiety, thus resulting in a decreased food intake. Woods et al., *Science* 1998, 280:1378-1383.

Another possible therapeutic effect associated with modulation of HSDs is that which is related to various pancreatic aliments. It is reported that inhibition of 11β-HSD1 in murine pancreatic β-cells results in increased insulin secretion. Davani et al., *J. Biol. Chem.* 2000, 275:34841-34844. This follows from the discovery that glucocorticoids were previously found to be responsible for reduced pancreatic insulin release in vivo, Billaudel et al., *Horm. Metab. Res.* 1979, 11:555-560. Thus, it is suggested that inhibition of 11β-HSD1 would yield other beneficial effects in the treatment of diabetes other than the predicted effects on the liver and fat reduction.

11β-HSD1 also regulates glucocorticoid activity in the brain and thus contributes to neurotoxicity. Rajan et al., *Neuroscience* 1996, 16:65-70; and Seckl et al., *Neuroendocrinol.* 2000, 18:49-99. Stress and/or glucocorticoids are known to influence cognitive function (de Quervain et al., *Nature* 1998, 394:787-790), and unpublished results indicate significant memory improvement in rats treated with a non-specific 11β-HSD inhibitor. These reports, in addition to the known effects of glucocorticoids in the brain, suggest that inhibiting HSDs in the brain may have a positive therapeutic effect against anxiety and related conditions. Tronche et al., *Nature Genetics* 1999, 23:99-103. 11β-HSD1 reactivates 11-DHC to corticosterone in hippocampal cells and can potentiate kinase neurotoxicity, resulting in age-related learning impairments. Therefore, selective inhibitors of 11β-HSD1 are believed to protect against hippocampal function decline with age. Yau et al., *Proc Natl. Acad. Sci. USA* 2001, 98:4716-4721. Thus, it has been hypothesized that inhibition of 11β-HSD1 in the human brain would protect against deleterious glucocorticoid-mediated effects on neuronal function, such as cognitive impairment, depression, and increased appetite.

HSDs are believed to play a role in immunomodulation based on the general perception that glucocorticoids suppress the immune system. There is known to be a dynamic interaction between the immune system and the HPA (hypothalamo-pituitary-adrenal) axis (Rook, *Baillier's Clin. Endocrinol. Metab.* 2000, 13: 576-581), and glucocorticoids help balance between cell-mediated responses and humoral responses. Increased glucocorticoid activity, which may be induced by stress, is associated with a humoral response and as such, the inhibition of 11β-HSD1 may result in shifting the response towards a cell-based reaction. In certain disease states, such as tuberculosis, leprosy, and psoriasis, the immune reaction is typically biased towards a humoral response when a cell-based response might be more appropriate. Inhibition of 11β-HSD1 is being studied for use to direct a cell-based response in these instances. Mason, *Immunology Today* 1991, 12:57-60. It follows then, that an alternative utility of 11β-HSD1 inhibition would be to bolster a temporal immune response in association with immunization to ensure that a cell based response would be obtained.

Recent reports suggest that the levels of glucocorticoid target receptors and of HSDs are connected with the risks of developing glaucoma. Stokes et al., *Invest. Ophthalmol.* 2000, 41:1629-1638. Further, a connection between inhibition of 11β-HSD1 and a lowering of the intraocular pressure was reported. Walker et al., poster P3-698 at the Endocrine society meeting Jun. 12-15, 1999, San Diego. It was shown that administration of the nonspecific 11β-HSD1 inhibitor, carbenoxolone, resulted in the reduction of the intraocular pressure by 20% in normal patients. In the eye, 11β-HSD1 is expressed exclusively in the basal cells of the corneal epithelium, the non-pigmented epithelialium of the cornea (the site of aqueous production), ciliary muscle, and the sphincter and dilator muscles of the iris. In contrast, the distant isoenzyme 11β-hydroxysteroid dehydrogenase type 2 ("11β-HSD2") is highly expressed in the non-pigmented ciliary epithelium and corneal endothelium. No HSDs have been found at the trabecular meshwork, which is the site of drainage. Therefore, 11β-HSD1 is suggested to have a role in aqueous production.

Glucocorticoids also play an essential role in skeletal development and function but are detrimental to such development and function when present in excess. Glucocorticoid-induced bone loss is partially derived from suppression of osteoblast proliferation and collagen synthesis, as reported in Kim et al., *J. Endocrinol.* 1999, 162:371 379. It has been reported that the detrimental effects of glucocorticoids on bone nodule formation can be lessened by administration of carbenoxolone, which is a non-specific 11β-HSD1 inhibitor. Bellows et al., *Bone* 1998, 23:119-125. Additional reports suggest that 11β-HSD1 may be responsible for providing increased levels of active glucocorticoid in osteoclasts, and thus in augmenting bone resorption. Cooper et al., *Bone* 2000, 27:375-381. This data suggests that inhibition of 11-HSD1 may have beneficial effects against osteoporosis via one or more mechanisms which may act in parallel.

It is known that bile acids inhibit 11β-HSD2 and that such inhibition results in a shift in the cortisol/cortisone equilibrium in the favor of cortisol. Quattropani et al., *J. Clin. Invest.* November 2001, 108:1299-305. A reduction in the hepatic activity of 11β-HSD2 is therefore predicted to reverse the cortisol/cortisone equilibrium to favor cortisone, which could provide therapeutic benefit in diseases such as hypertension.

The various isozymes of the 17-beta-hydroxysteroid dehydrogenases (17β-HSDs) bind to androgen receptors or estrogen receptors and catalyze the interconversion of various sex hormones including estradiol/estrone and testosterone/androstenedione. To date, six isozymes have been identifed in humans and are expressed in various human tissues including endometrial tissue, breast tissue, colon tissue, and in the testes. 17-beta-Hydroxysteroid dehydrogenase type 2 (17β-HSD2) is expressed in human endometrium and its activity has been reported to be linked to cervical cancer. Kitawaki et al., *J. Clin. Endocrin. Metab.*, 2000, 85:1371-3292-3296. 17-beta-Hydroxysteroid dehydrogenase type 3 (17β-HSD3) is expressed in the testes and its modulation may be useful for the treatment of androgen-related disorders.

Androgens and estrogens are active in their 17β-hydroxy configurations, whereas their 17-keto derivatives do not bind to androgen and estrogen receptors and are thus inactive. The conversion between the active and inactive forms (estradiol/estrone and testosterone/androstenedione) of sex hormones is catalyzed by members of the 17β-HSD family. 17β-HSD1 catalyzes the formation of estradiol in breast tissue, which is important for the growth of malignant breast tumors. Labrie et al., *Mol. Cell. Endocrinol.* 1991, 78: C113-C118. A similar role has been suggested for 17β-HSD4 in colon cancer. English et al., *J. Clin. Endocrinol. Metab.* 1999, 84:2080-2085. 17β-HSD3 is almost exclusively expressed in the testes and converts androstenedione into testosterone. Deficiency of this enzyme during fetal development leads to male pseudohermaphroditism. Geissler et al., *Nat. Genet.* 1994, 7:34-39. Both 17β-HSD3 and various 3α-HSD isozymes are involved in complex metabolic pathways which lead to androgen shuffles between inactive and active forms. Penning et al., *Biochem. J.* 2000, 351:67-77. Thus, modulation of certain HSDs can have potentially beneficial effects in the treatment of androgen- and estrogen-related disorders.

The 20-alpha-hydroxysteroid dehydrogenases (20α-HSDs) catalyze the interconversion of progestins (such as between progesterone and 20α-hydroxy progesterone). Other substrates for 20α-HSDs include 17α-hydroxypregnenolone or 17α-hydroxyprogesterone, leading to 20α-OH steroids. Several 20α-HSD isoforms have been identified and 20α-HSDs are expressed in various tissues, including the placenta, ovaries, testes and adrenals. Peltoketo, et al., *J. Mol. Endocrinol.* 1999, 23:1-11.

The 3-alpha-hydroxysteroid dehydrogenases (3α-HSDs) catalyze the interconversion of the androgens dihydrotestosterone (DHT) and 5α-androstane-3α, 17β-diol and the interconversion of the androgens DHEA and androstenedione and therefore play an important role in androgen metabolism. Ge et al., *Biology of Reproduction* 1999, 60:855-860.

Despite the previous research done in the field of HSD inhibition, there remains a need for novel compounds that are potent inhibitors of the various families of HSDs and efficacious for the treatment of HSD-mediated conditions such as diabetes, obesity, glaucoma, osteoporosis, cognitive disorders, immune disorders, depression, hypertension, and others.

BRIEF SUMMARY OF THE INVENTION

The present invention satisfies this need and others by providing novel compounds, compositions thereof and methods for modulating the activity of hydroxysteroid dehydrogenases (HSDs), such as 11β-hydroxysteroid dehydrogenases, 17β-hydroxysteroid dehydrogenases, 20α-hydroxysteroid dehydrogenases, and 3α-hydroxysteroid dehydrogenases, including all isoforms thereof, including but not limted to 11β-hydroxysteroid dehydrogenase type 1 (hereinafter "11β-HSD1"), 11β-hydroxysteroid dehydrogenase type 2 (hereinafter "11β-HSD2"), and 17β-hydroxysteroid dehydrogenase type 3 (hereinafter "17β-HSD3"). In one embodiment, the compounds of the invention inhibit HSD activity.

The present invention also relates to methods for treating or preventing diseases or disorders associated with the action of hydroxysteroid dehydrogenases, comprising administering to a patient in need thereof a therapeutically effective amount of an aniline sulfonamide derivative of formula I or a pharmaceutically acceptable salt, solvate, stereoisomer, or prodrug thereof. The invention encompasses both selective and non-selective inhibitors of hydroxysteroid dehydrogenases.

It should be understood that selective and non-selective inhibitors of hydroxysteroid dehydrogenases each have benefits in the treatment or prevention of diseases associated with, for example, abnormal glucose levels or hypothalmic function. The invention also encompasses selective inhibitors of HSDs. Two types of selectivity are contemplated, that with respect to selectivity for HSDs as a class over other types of receptors or gene targets related to glucose metabolism, or those which are selective for various HSDs or specific isoforms thereof compared to other HSDs or specific isoforms thereof.

In one embodiment, the aniline sulfonamide derivatives can act as selective or non-selective 11β-HSD inhibitors. The compounds may inhibit the interconversion of inactive 11-keto steroids with their active hydroxy equivalents. The present invention provides methods by which the conversion of the inactive to the active form may be controlled, and useful therapeutic effects which may be obtained as a result of such control. More specifically, but not exclusively, the invention is concerned with interconversion between cortisone and cortisol in humans.

In another embodiment, the aniline sulfonamide derivatives can act as 11β-HSD inhibitors in vivo.

In another embodiment, the aniline sulfonamide derivatives of the present invention may be orally active.

The aniline sulfonamide derivatives are also useful for the modulation of numerous metabolic functions including, but not limited to, one or more of: (i) regulation of carbohydrate metabolism, (ii) regulation of protein metabolism, (iii) regulation of lipid metabolism, (iv) regulation of normal growth and/or development, (v) influence on cognitive function, (vi) resistance to stress and mineralocorticoid activity.

The aniline sulfonamide derivatives are additionally useful for inhibiting hepatic gluconeogenesis, and they also can be effective to relieve the effects of endogenous glucocorticoids in diabetes mellitus, obesity (including entripetal obesity), neuronal loss and/or the cognitive impairment of old age. Thus, in a further aspect, the invention provides the use of an inhibitor of HSDs in methods directed to producing one or more therapeutic effects in a patient to whom the aniline sulfonamide derivative is administered, said therapeutic effects selected from the group consisting of inhibition of hepatic gluconeogenesis, an increase in insulin sensitivity in adipose tissue and muscle, and the prevention of or reduction in neuronal loss/cognitive impairment due to glucocorticoid-potentiated neurotoxicity or neural dysfunction or damage.

The invention further provides methods for treating a condition selected from the group consisting of: hepatic insulin resistance, adipose tissue insulin resistance, muscle insulin resistance, neuronal loss or dysfunction due to glucocorticoid potentiated neurotoxicity, and any combination of the aforementioned conditions, the methods comprising administering to a patient in need thereof a therapeutically effective amount of an aniline sulfonamide derivative.

The aniline sulfonamide derivatives of the invention are compounds having Formula I as well as pharmaceutically acceptable salts, solvates, stereoisomers, or prodrugs thereof.

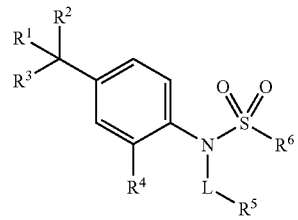

(I)

In formula I, $R^1$ is a member selected from the group consisting of —OH, halogen and $(C_1-C_8)$haloalkyl. $R^2$ is selected from the group consisting of $(C_1-C_8)$alkyl, $(C_2-C_8)$alkenyl, $(C_2-C_8)$alkynyl, $(C_1-C_8)$alkoxy, $(C_1-C_8)$haloalkyl, $(C_2-C_8)$hydroxyalkyl and $(C_3-C_8)$cycloalkyl. $R^3$ is selected from the group consisting of halogen, $(C_1-C_8)$alkyl, $(C_2-C_8)$alkenyl, $(C_2-C_8)$alkynyl, $(C_1-C_8)$alkoxy, $(C_2-C_8)$hydroxyalkyl and $(C_3-C_8)$cycloalkyl.

Substituent $R^4$ is a member selected from the group consisting of hydrogen, halogen, $(C_1-C_8)$alkyl and $(C_3-C_8)$cycloalkyl.

Substituent $R^5$ is selected from the group consisting of hydrogen, —OH, halogen, $(C_1-C_8)$alkyl, $(C_1-C_8)$haloalkyl, $(C_2-C_8)$heteroalkyl as defined below, $(C_3-C_8)$cycloalkyl, $(C_3-C_8)$heterocycloalkyl, C(O)R', C(O)NR'$_2$, NR'$_2$, NR'C(O)R', CN, NO$_2$, aryl, and heteroaryl.

In one embodiment, $R^6$ may be combined with $R^5$ to form a 5- to 6-membered fused ring containing L if it is present, the nitrogen atom to which $R^5$ is attached, and the sulfur to which $R^6$ is attached.

Variable L is selected from the group consisting of a direct bond, $(C_1-C_4)$alkylene and $(C_2-C_4)$alkenylene as defined below.

In the embodiments described herein, any cycloalkyl portion, heterocycloalkyl portion, aryl or heteroaryl portion can be substituted from one to four members selected from the group consisting of halogen, —CN, —NO$_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $(C_2-C_8)$hydroxyalkyl, —C(O)R', —C(O)OR', —NR'C(O)OR", —OR', —SR', —OC(O)R', —C(O)N(R')$_2$, —S(O)R", —SO$_2$R", —SO$_2$N(R')$_2$, —N(R')$_2$ and —NR'C(O)R'.

Each occurrence of R' is independently H or an unsubstituted member selected from the group consisting of $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_2-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, and aryl$(C_1-C_6)$alkyl. In some embodiments, two R' groups, when they attached to the same nitrogen atom, can be combined with the nitrogen atom to which they are attached to form a heterocycle or heteroaryl group.

Each occurrence of R" is independently an unsubstituted member selected from the group consisting of $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_2-C_8)$hydroxyalkyl, $(C_3-C_8)$cycloalkyl, $(C_3-C_8)$heterocycloalkyl, heteroaryl, aryl, $(C_3-C_8)$cycloalkyl $(C_1-C_6)$alkyl, heterocyclyl$(C_1-C_6)$alkyl, heteroaryl$(C_1-C_6)$alkyl and aryl$(C_1-C_6)$alkyl.

One embodiment of the invention provides a pharmaceutical composition comprising an aniline sulfonamide derivative of Formula (I) and a pharmaceutically acceptable vehicle, carrier, excipient or diluent.

In another embodiment, the invention provides methods for treating insulin-dependent diabetes mellitus comprising administering to a patient in need thereof a therapeutically effective amount of an aniline sulfonamide derivative derivative of Formula (I).

In another embodiment, the invention provides methods for treating non-insulin-dependent diabetes mellitus comprising administering to a patient in need thereof a therapeutically effective amount of an aniline sulfonamide derivative of Formula (I).

In yet another embodiment, the invention provides a method for treating insulin resistance comprising administering to a patient in need thereof a therapeutically effective amount of an aniline sulfonamide derivative of Formula (I).

In still another embodiment, the invention provides a method for treating obesity comprising administering to a patient in need thereof a therapeutically effective amount of an aniline sulfonamide derivative of Formula (I).

In another embodiment, the invention provides a method for modulating cortisol production comprising administering to a patient in need thereof a therapeutically effective, amount of an aniline sulfonamide derivative of Formula (I).

In another embodiment, the invention provides methods for modulating hepatic glucose production comprising administering to a patient in need thereof a therapeutically effective amount of an aniline sulfonamide derivative of Formula (I).

In another embodiment, the invention provides a method for modulating hypothalamic function comprising administering to a patient in need thereof a therapeutically effective amount of an aniline sulfonamide derivative of Formula (I).

In one embodiment, the invention provides a method for treating a hydroxysteroid dehydrogenase-mediated condition or disorder comprising administering to a patient in need thereof a therapeutically effective amount of an aniline sulfonamide derivative of Formula (I).

In another embodiment, the invention provides a method for modulating the function of a hydroxysteroid dehydrogenase in a cell comprising administering to a patient in need thereof a therapeutically effective amount of an aniline sulfonamide derivative of Formula (I).

In a further embodiment, the invention provides a method for modulating a hydroxysteroid dehydrogenase, comprising administering to a patient in need thereof a therapeutically effective amount of an aniline sulfonamide derivative of Formula (I).

In still another embodiment, the invention provides a method for treating an 11β-HSD1-mediated condition or disorder comprising administering to a patient in need thereof a therapeutically effective amount of an aniline sulfonamide derivative of Formula (I).

In yet another embodiment, the invention provides a method for modulating the function of 11β-HSD1 in a cell comprising administering to a patient in need thereof a therapeutically effective amount of an aniline sulfonamide derivative of Formula (I).

In a further embodiment, the invention provides a method for modulating 11β-HSD1, comprising administering to a patient in need thereof a therapeutically effective amount of an aniline sulfonamide derivative of Formula (I).

In one embodiment, the invention provides a method for treating an 11β-HSD2-mediated condition or disorder comprising administering to a patient in need thereof a therapeutically effective amount of an aniline sulfonamide derivative of Formula (I).

In another embodiment, the invention provides a method for modulating the function of 11β-HSD2 in a cell comprising administering to a patient in need thereof a therapeutically effective amount of an aniline sulfonamide derivative of Formula (I).

In a further embodiment, the invention provides a method for modulating 11β-HSD2, comprising administering to a patient in need thereof a therapeutically effective amount of an aniline sulfonamide derivative of Formula (I).

In one embodiment, the invention provides a method for treating an 17β-HSD3-mediated condition or disorder comprising administering to a patient in need thereof a therapeutically effective amount of an aniline sulfonamide derivative of Formula (I).

In another embodiment, the invention provide a method for modulating the function of 17β-HSD3 in a cell comprising administering to a patient in need thereof a therapeutically effective amount of an aniline sulfonamide derivative of Formula (I).

In a further embodiment, the invention provides a method for modulating 17β-HSD3, comprising administering to a patient in need thereof a therapeutically effective amount of an aniline sulfonamide derivative of Formula (I).

These and other embodiments of this invention will be evident upon reference to the following detailed description. To that end, certain patent and other documents are cited herein to more specifically set forth various embodiments of this invention. Each of these documents are hereby incorporated by reference in their entireties.

DETAILED DESCRIPTION OF THE INVENTION

Definitions

As used herein, the terms have the following meanings:

The term "alkyl" as used herein refers to a straight or branched chain, saturated hydrocarbon having the indicated number of carbon atoms. For example, $(C_1-C_6)$alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein below.

The term "alkenyl" as used herein refers to a straight or branched chain unsaturated hydrocarbon having the indicated number of carbon atoms and at least one double bond. Examples of a $(C_2-C_8)$alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" as used herein refers to a straight or branched chain unsaturated hydrocarbon having the indicated number of carbon atoms and at least one triple bond. Examples of a $(C_2-C_8)$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkylene" refers to a divalent alkyl group (e.g., an alkyl group attached to two other moieties, typically as a linking group). Examples of a $(C_1-C_7)$alkylene include —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, and —CH₂CH₂CH₂CH₂CH₂CH₂CH₂—, as well as branched versions thereof. An alkylene group can be unsubstituted or optionally substituted with one or more substituents as described herein below.

The term "alkenylene" refers to a divalent alkene group (e.g., an alkene group attached to two other moieties, typically as a linking group). Examples of a $(C_2-C_7)$alkenylene include —CH=CH—, —CH=CHCH₂—, —CH=CHCH₂CH₂—, —CH=CHCH₂CH₂CH₂—, —CH=CHCH₂CH₂CH₂CH₂—, and —CH=CHCH₂CH₂CH₂CH₂CH₂—, as well as branched versions and structure isomers thereof. An alkenylene group can be unsubstituted or optionally substituted with one or more substituents as described herein below.

The term "alkoxy" as used herein refers to an —O-alkyl group having the indicated number of carbon atoms. For example, a $(C_1-C_6)$alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl," as used herein, refers to an alkyl group (typically one to six carbon atoms) wherein from one or more of the $C_1-C_6$ alkyl group's hydrogen atoms is replaced with an amine of formula —N(R$^a$)₂, wherein each occurrence of R$^a$ is independently —H or $(C_1-C_6)$alkyl. Examples of aminoalkyl groups include, but are not limited to, —CH₂NH₂, —CH₂CH₂NH₂—, —CH₂CH₂CH₂NH₂, —CH₂CH₂CH₂CH₂NH₂, —CH₂CH₂CH₂CH₂CH₂NH₂, —CH₂CH₂CH₂CH₂CH₂CH₂NH₂, —CH₂CH₂CH₂N(CH₃)₂, t-butylaminomethyl, isopropylaminomethyl and the like.

The term "aryl" as used herein refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein below.

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene. A cycloalkyl group can be unsubstituted or optionally substituted with one or more substituents as described herein below.

The term "halo" as used herein refers to —F, —Cl, —Br or —I.

The term "haloalkyl," as used herein, refers to a $C_1-C_6$ alkyl group wherein from one or more of the $C_1-C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any position of the heteroalkyl group. Examples include —CH₂—CH₂—O—CH₃, —CH₂—CH₂—NH—CH₃, —CH₂—CH₂—N(CH₃)—CH₃, —CH₂—S—CH₂—CH₃, —CH₂—CH₂—S(O)—CH₃, —CH₂—CH₂—S(O)₂—CH₃, and —CH₂—CH=N—OCH₃. Up to two heteroatoms may be consecutive, such as, for example, —CH₂—NH—OCH₃. When a prefix such as $(C_2-C_8)$ is used to refer to a heteroalkyl group, the number of carbons (2 to 8, in this example) is meant to include the heteroatoms as well. For example, a $C_2$-heteroalkyl group is meant to include, for example, —CH₂OH (one carbon atom and one heteroatom replacing a carbon atom) and —CH₂SH.

To further illustrate the definition of a heteroalkyl group, where the heteroatom is oxygen, a heteroalkyl group is an oxyalkyl group. For instance, $(C_2-C_5)$oxyalkyl is meant to include, for example —CH₂—O—CH₃ (a $C_3$-oxyalkyl group with two carbon atoms and one oxygen replacing a carbon atom), —CH₂CH₂CH₂CH₂OH, and the like.

The term "heteroalkylene" by itself or as part of another substituent means a divalent radical derived from heteroalkyl, as exemplified by —CH₂—CH₂—S—CH₂CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl". Thus, the term "heterocycloalkyl" is meant to be included in the term "heteroalkyl". Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

Substituents for the alkyl radicals (as well as those groups referred to as alkylene, alkenyl, alkynyl, cycloalkyl, heterocycloalkyl, cycloalkenyl and heterocycloalkenyl) can be a variety of groups selected from: —OR', =O, =NR', =N—OR', —NR'R", —SR', -halo, —SiR'R"R'", —OC(O)R', —C(O)R', —CO$_2$R', —CONR'R", —OC(O)NR'R", —NR"C(O)R', —NR'"C(O)NR'R", —NR'"SO$_2$NR'R", —NR"CO$_2$R', —NHC(NH$_2$)=NH, —NR'C(NH$_2$)=NH, —NHC(NH$_2$)=NR', —S(O)R', —SO$_2$R', —SO$_2$NR'R", —NR"SO$_2$R', —CN and —NO$_2$, in a number ranging from zero to three, with those groups having zero, one or two substituents being exemplary. R', R" and R'" each independently refer to hydrogen, unsubstituted (C$_1$-C$_8$)alkyl, unsubstituted hetero(C$_1$-C$_8$)alkyl, unsubstituted aryl and aryl substituted with one to three substituents selected from -halo, unsubstituted alkyl, unsubstituted alkoxy, unsubstituted thioalkoxy and unsubstituted aryl(C$_1$-C$_4$)alkyl. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Exemplary substituents for the alkyl and heteroalkyl radicals include but are not limited to —OR', =O, —NR'R", —SR', -halo, —SiR'R"R'", —OC(O)R', -C(O)R', —CO$_2$R', —C(O)NR'R", —OC(O)NR'R", —NR"C(O)R', —NR"CO$_2$R', —NR'"SO$_2$NR'R", —S(O)R', —SO$_2$R', —SO$_2$NR'R", —NR"SO$_2$R', —CN and —NO$_2$, where R', R" and R'" are as defined above. Typical substituents can be selected from: —OR', =O, —NR'R", -halo, —OC(O)R', —CO$_2$R', —C(O)NR'R", —OC(O)NR'R", —NR"C(O)R', —NR"CO$_2$R', —NR'"SO$_2$NR'R", —SO$_2$R', —SO$_2$NR'R", —NR"SO$_2$R'—CN and —NO$_2$.

Similarly, substituents for the aryl and heteroaryl groups are varied and selected from: -halo, —OR', —OC(O)R', —NR'R", —SR', —R', —CN, —NO$_2$, —CO$_2$R', —C(O)NR'R", —C(O)R', —OC(O)NR'R", —NR"C(O)R', —NR"CO$_2$R', —NR"C(O)NR'R", —NR'"SO$_2$NR'R", —NHC(NH$_2$)=NH, —NR'C(NH$_2$)=NH, —NH—C(NH$_2$)=NR', —S(O)R', —SO$_2$R', —SO$_2$NR'R", —NR"SO$_2$R', —N$_3$, —CH(Ph)$_2$, perfluoroalkoxy and perfluoro(C$_1$-C$_4$)alkyl, in a number ranging from zero to the total number of open valences on the aromatic ring system; and where R', R" and R'" are independently selected from hydrogen, unsubstituted (C$_1$-C$_8$)alkyl, unsubstituted hetero(C$_1$-C$_8$)alkyl, unsubstituted aryl, unsubstituted heteroaryl, unsubstituted aryl(C$_1$-C$_4$)alkyl and unsubstituted aryloxy(C$_1$-C$_4$)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of the aryl or heteroaryl ring in an aryl or heteroaryl group may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$-X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

It is to be understood that the substituent —CO$_2$H, as used herein, may be optionally replaced with bioisosteric replacements such as:

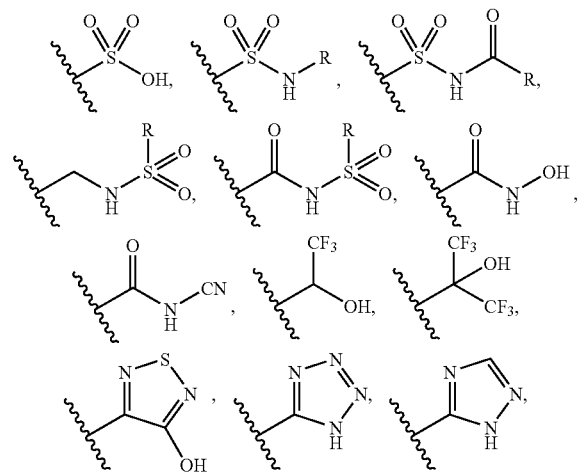

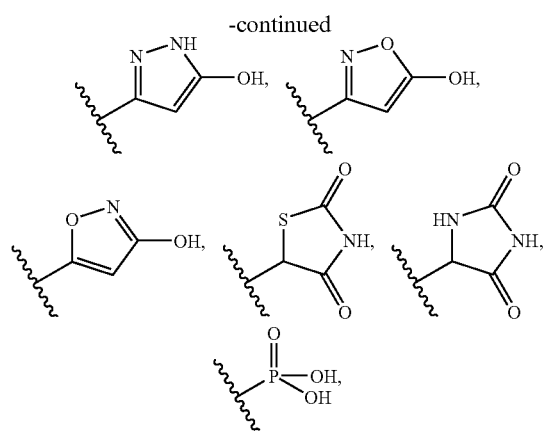

and the like. See, e.g., *The Practice of Medicinal Chemistry*; Wermuth, C. G., Ed.; Academic Press: New York, 1996; p. 203.

The aniline sulfonamide derivative of formula I can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of an aniline sulfonamide derivative, including tautomeric forms of the compound.

Certain aniline sulfonamide derivatives may have asymmetric centers and therefore exist in different enantiomeric and diastereomeric forms. An aniline sulfonamide derivative can be in the form of an optical isomer or a diastereomer. Accordingly, the invention encompasses aniline sulfonamide derivatives and their uses as described herein in the form of their optical isomers, diasteriomers and mixtures thereof, including racemic mixtures. Optical isomers of the aniline sulfonamide derivatives can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of it.

An aniline sulfonamide derivative can be in the form of a pharmaceutically acceptable salt. Depending on the structure of the derivative, the phrase "pharmaceutically acceptable salt," as used herein, refers to a pharmaceutically acceptable organic or inorganic acid or base salt of an aniline sulfonamide derivative. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Hence, a pharmaceutically acceptable salt can have one or more charged atoms and/or one or more counterions.

As used herein, the term "isolated and purified form" means that when isolated (e.g., from other components of a synthetic organic chemical reaction mixture), the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of an aniline sulfonamide derivative by weight of the isolate. In one embodiment, the isolate contains at least 95% of an aniline sulfonamide derivative by weight of the isolate.

As used herein, the term "prodrug" means a derivative of a compound that can hydrolyze, oxidize, or otherwise react under biological conditions (in vitro or in vivo) to provide an active compound, particularly an aniline sulfonamide derivative. Examples of prodrugs include, but are not limited to, derivatives and metabolites of an aniline sulfonamide derivative that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). In some embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein, the terms "treat", "treating" and "treatment" refer to the eradication or amelioration of a disease or symptoms associated with a disease. In certain embodiments, such terms refer to minimizing the spread or worsening of the disease resulting from the administration of one or more prophylactic or therapeutic agents to a patient with such a disease.

As used herein, the terms "prevent", "preventing" and "prevention" refer to the prevention of the onset, recurrence or spread of the disease in a patient resulting from the administration of a prophylactic or therapeutic agent.

The term "effective amount" as used herein refers to an amount of an aniline sulfonamide derivative or other active ingredient sufficient to provide a therapeutic or prophylactic benefit in the treatment or prevention of a disease or to delay or minimize symptoms associated with a disease. Further, a therapeutically effective amount with respect to an aniline sulfonamide derivative means that amount of therapeutic agent alone, or in combination with other therapies, that provides a therapeutic benefit in the treatment or prevention of a disease. Used in connection with an aniline sulfonamide derivative, the term can encompass an amount that improves overall therapy, reduces or avoids symptoms or causes of disease, or enhances the therapeutic efficacy of or synergies with another therapeutic agent.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

The terms "modulate", "modulation" and the like refer to the ability of a compound to increase or decrease the function, or activity of, for example, 11β-HSD1. "Modulation", as used herein in its various forms, is intended to encompass inhibition, antagonism, partial antagonism, activation, agonism and/or partial agonism of the activity associated with 11β-HSD1. 11β-HSD1 inhibitors are compounds that, e.g., bind to, partially or totally block stimulation, decrease, prevent, delay activation, inactivate, desensitize, or down regulate signal transduction. 11β-HSD1 activators are compounds that, e.g., bind to, stimulate, increase, open, activate, facilitate, enhance activation, sensitize or up regulate signal transduction. The ability of a compound to modulate 11β-HSD1 can be demonstrated in an enzymatic assay or a cell-based assay. For example, the inhibition of 11β-HSD1 may decrease cortisol levels in a patient and/or increase cortisone levels in a patient by blocking the conversion of cortisone to cortisol. Alternatively, the inhibition of 11β-HSD2 can increase cortisol levels in a patient and/or decrease cortisone levels in a patient by blocking the conversion of cortisol to cortisone.

A "patient" includes an animal (e.g., cow, horse, sheep, pig, chicken, turkey, quail, cat, dog, mouse, rat, rabbit or guinea pig), in one embodiment a mammal such as a non-primate or a primate (e.g., monkey and human), and in another embodiment a human. In a one embodiment, a patient is a human. In other embodiments, the patient is a human infant, child, adolescent or adult.

The term "HSD" as used herein, refers to hydroxysteroid dehydrogenase enzymes in general, including, but not limited to, 11-beta-hydroxysteroid dehydrogenases (11β-HSDs), 17-beta-hydroxysteroid dehydrogenases (17β-HSDs), 20-alpha-hydroxysteroid dehydrogenases (20α-HSDs), 3-alpha-hydroxysteroid dehydrogenases (3α-HSDs), and all isoforms thereof.

The term "11β-HSD1" as used herein, refers to the 11-beta-hydroxysteroid dehydrogenase type 1 enzyme, variant, or isoform thereof. 11β-HSD1 variants include proteins substantially homologous to native 11β-HSD1, i.e., proteins having one or more naturally or non-naturally occurring amino acid deletions, insertions or substitutions (e.g., 11β-HSD1 derivatives, homologs and fragments). The amino acid sequence of a 11β-HSD1 variant can be at least about 80% identical to a native 11β-HSD1, or at least about 90% identical, or at least about 95% identical.

The term "11β-HSD2" as used herein, refers to the 11-beta-hydroxysteroid dehydrogenase type 2 enzyme, variant, or isoform thereof. 11β-HSD2 variants include proteins substantially homologous to native 11β-HSD2, i.e., proteins having one or more naturally or non-naturally occurring amino acid deletions, insertions or substitutions (e.g., 11β-HSD2 derivatives, homologs and fragments). The amino acid sequence of a 11β-HSD2 variant can be at least about 80% identical to a native 11β-HSD2, or at least about 90% identical, or at least about 95% identical. (see Bart et al., *J. Med. Chem.*, 2002, 45:3813-3815).

The term "17β-HSD3" as used herein, refers to the 17-beta-hydroxysteroid dehydrogenase type 3 enzyme, variant, or isoform thereof. 17β-HSD3 variants include proteins substantially homologous to native 17β-HSD3, i.e., proteins having one or more naturally or non-naturally occurring amino acid deletions, insertions or substitutions (e.g., 17β-HSD3 derivatives, homologs and fragments). The amino acid sequence of a 17β-HSD3 variant can be at least about 80% identical to a native 17β-HSD3, or at least about 90% identical, or at least about 95% identical.

As used herein, the term "HSD-responsive condition or disorder" and related terms and phrases refer to a condition or disorder that responds favorably to modulation of a hydroxysteroid dehydrogenase enzyme (HSD). Favorable responses to HSD modulation include alleviation or abrogation of the disease and/or its attendant symptoms, inhibition of the disease, i.e., arrest or reduction of the development of the disease, or its clinical symptoms, and regression of the disease or its clinical symptoms. An HSD-responsive condition or disease may be completely or partially responsive to HSD modulation. An HSD-responsive condition or disorder may be associated with inappropriate, e.g., less than or greater than normal, HSD activity and at least partially responsive to or affected by HSD modulation (e.g., an HSD inhibitor results in some improvement in patient well-being in at least some patients). Inappropriate HSD functional activity might arise as the result of HSD expression in cells which normally do not express HSD, decreased HSD expression or increased HSD expression. An HSD-responsive condition or disorder may include condition or disorder mediated by any HSD or isoform thereof.

As used herein, the term "11β-HSD1-responsive condition or disorder" and related terms and phrases refer to a condition or disorder that responds favorably to modulation of 11β-HSD1 activity. Favorable responses to 11β-HSD1 modulation include alleviation or abrogation of the disease and/or its attendant symptoms, inhibition of the disease, i.e., arrest or reduction of the development of the disease, or its clinical symptoms, and regression of the disease or its clinical symptoms. An 11β-HSD1-responsive condition or disease may be completely or partially responsive to 11β-HSD1 modulation. An 11β-HSD1-responsive condition or disorder may be associated with inappropriate, e.g., less than or greater than normal, 11β-HSD1 activity and at least partially responsive to or affected by 11β-HSD1 modulation (e.g., a 11β-HSD1 inhibitor results in some improvement in patient well-being in at least some patients). Inappropriate 11β-HSD1 functional activity might arise as the result of 11β-HSD1 expression in cells which normally do not express 11β-HSD1, decreased 11β-HSD1 expression or increased 11β-HSD1 expression. A 11β-HSD1-responsive condition or disorder may include a 11β-HSD1-mediated condition or disorder.

As used herein, the term "11β-HSD2-responsive condition or disorder" and related terms and phrases refer to a condition or disorder that responds favorably to modulation of 11β-HSD2 activity. Favorable responses to 11β-HSD2 modulation include alleviation or abrogation of the disease and/or its attendant symptoms, inhibition of the disease, i.e., arrest or reduction of the development of the disease, or its clinical symptoms, and regression of the disease or its clinical symptoms. An 11β-HSD2-responsive condition or disease may be completely or partially responsive to 11β-HSD2 modulation. An 11β-HSD2-responsive condition or disorder may be associated with inappropriate, e.g., less than or greater than normal, 11β-HSD2 activity and at least partially responsive to or affected by 11β-HSD2 modulation (e.g., a 11β-HSD2 inhibitor results in some improvement in patient well-being in at least some patients).

As used herein, the term "17β-HSD3-responsive condition or disorder" and related terms and phrases refer to a condition or disorder that responds favorably to modulation of 17β-HSD3 activity. Favorable responses to 17β-HSD3 modulation include alleviation or abrogation of the disease and/or its attendant symptoms, inhibition of the disease, i.e., arrest or reduction of the development of the disease, or its clinical symptoms, and regression of the disease or its clinical symptoms. An 17β-HSD3-responsive condition or disease may be completely or partially responsive to 17β-HSD3 modulation. An 17β-HSD3-responsive condition or disorder may be associated with inappropriate, e.g., less than or greater than normal, 17β-HSD3 activity and at least partially responsive to or affected by 17β-HSD3 modulation (e.g., a 17β-HSD3 inhibitor results in some improvement in patient well-being in at least some patients). Inappropriate 17β-HSD3 functional activity might arise as the result of 17β-HSD3 expression in cells which normally do not express 17β-HSD3, decreased 17β-HSD3 expression or increased 17β-HSD3 expression. A 17β-HSD3-responsive condition or disorder may include a 17β-HSD3-mediated condition or disorder.

As used herein, the term "HSD-mediated condition or disorder" and related terms and phrases refer to a condition or disorder characterized by inappropriate, e.g., less than or greater than normal, activity of a hydroxysteroid dehydrogenase (HSD). An HSD-mediated condition or disorder may be completely or partially characterized by inappropriate HSD activity. However, an HSD-mediated condition or disorder is one in which modulation of an HSD results in some effect on the underlying condition or disease (e.g., an HSD inhibitor results in some improvement in patient well-being in at least some patients).

As used herein, the term "11β-HSD1-mediated condition or disorder" and related terms and phrases refer to a condition or disorder characterized by inappropriate, e.g., less than or greater than normal, 11β-HSD1 activity. A 11β-HSD1-mediated condition or disorder may be completely or partially characterized by inappropriate 11β-HSD1 activity. However, a 11β-HSD1-mediated condition or disorder is one in which modulation of 11β-HSD1 results in some effect on the underlying condition or disease (e.g., a 11β-HSD1 inhibitor results in some improvement in patient well-being in at least some patients).

As used herein, the term "11β-HSD2-mediated condition or disorder" and related terms and phrases refer to a condition or disorder characterized by inappropriate, e.g., less than or greater than normal, 11β-HSD2 activity. A 11β-HSD2-mediated condition or disorder may be completely or partially characterized by inappropriate 11β-HSD2 activity. However, a 11β-HSD2-mediated condition or disorder is one in which modulation of 11β-HSD2 results in some effect on the underlying condition or disease (e.g., a 11β-HSD2 inhibitor results in some improvement in patient well-being in at least some patients).

As used herein, the term "17β-HSD3-mediated condition or disorder" and related terms and phrases refer to a condition or disorder characterized by inappropriate, e.g., less than or greater than normal, 17β-HSD3 activity. A 17β-HSD3-mediated condition or disorder may be completely or partially characterized by inappropriate 17β-HSD3 activity. However, a 17β-HSD3-mediated condition or disorder is one in which modulation of 17β-HSD3 results in some effect on the underlying condition or disease (e.g., a 17β-HSD3 inhibitor results in some improvement in patient well-being in at least some patients).

The following abbreviations are used herein and have the indicated definitions: DMEM is Dulbecco's Modified Eagle Medium; Et₃N is triethylamine; EtOAc is ethyl acetate; MeOH is methanol; MS is mass spectrometry; NMR is nuclear magnetic resonance; PBS is phosphate-buffered saline; SPA is scintillation proximity assay; THF is tetrahydrofuran; and TMS is trimethylsilyl.

Compounds of the Invention

The present invention provides compounds of Formula (I) as well as their pharmaceutically acceptable salts, solvates, stereoisomers, or prodrugs thereof, collectively referred to as the "The aniline sulfonamide derivatives."

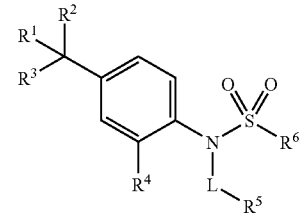

(I)

Variables $R^1$, $R^2$, $R^3$, $R^4$, $R^5$, $R^6$, and L are defined as set forth above in the summary of the invention.

In combination with any of the embodiments described herein, one embodiment provides for L being a direct bond.

In other embodiments, $R^5$ is $(C_1-C_8)$alkyl. For example, $R^5$ can be a $(C_1-C_3)$alkyl. Specific examples of $R^5$ include but are not limited to methyl, ethyl, and isopropyl. In one embodiment, $R^5$ is isopropyl.

In yet other embodiments, $R^5$ is $(C_3-C_8)$cycloalkyl. Specific $(C_3-C_8)$cycloalkyl groups include but are not limited to cyclopropyl and cyclobutyl.

Other embodiments provide for $R^6$ being aryl. In some embodiments, $R^6$ is aryl optionally substituted with one to four substiuents. Thus, for example, $R^6$ can be dichloro-substituted phenyl, 2-chloro-5-cyano-phenyl, 2-chloro-phenyl, or 2-chloro-5-trifluoromethyl-phenyl.

In further embodiments, $R^5$ is selected from $(C_1-C_8)$alkyl and halo-$(C_1-C_8)$alkyl, and $R^6$ is selected from phenyl and substituted phenyl. For example, $R^5$ can be selected from methyl, ethyl and isopropyl and $R^6$ can be halosubstitued phenyl or CN-substituted phenyl.

In other embodiments, $R^5$ is a $C_3-C_8$ cycloalkyl moiety and $R^6$ is selected from phenyl and substituted phenyl. In these embodiments, $R^5$ can be cyclopropyl or cyclobutyl.

In some embodiments, optionally in combination with any other embodiment described herein, $R^1$ is —OH.

In still other embodiments, $R^2$ is $(C_1-C_8)$haloalkyl and and $R^3$ is $(C_1-C_8)$alkyl. For example, the $(C_1-C_8)$haloalkyl group can be trifluoromethyl. Illustrative of a $(C_1-C_8)$alkyl group is methyl.

Further embodiments provide for compounds wherein $R^1$ is —OH, and wherein $R^2$ is trifluoromethyl and $R^3$ is methyl. Specific examples satisfying these structural requirements are wherein $R^1$, $R^2$, and $R^3$, together with the carbon atom to which they are attached, are an (S)-trifluoromethyl carbinol group of the formula:

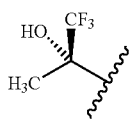

Alternatively, $R^1$, $R^2$, and $R^3$, together with the carbon atom to which they are attached, are an (R)-trifluoromethyl carbinol group of the formula:

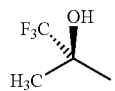

The aniline sulfonamide derivatives can have asymmetric centers and therefore exist in different enantiomeric and diastereomeric forms. This invention relates to the use of all optical isomers and stereoisomers of the aniline sulfonamide derivatives, and mixtures thereof, and to all pharmaceutical compositions and methods of treatment that may employ or contain them.

It should be noted that racemates, racemic mixtures, and stereoisomers, particularly diastereomeric mixtures or diastereomerically pure compounds and enantiomers or enantiomerically pure compounds of the above are all contemplated.

Specific examples of compounds of Formula I are provided below:

| Example | Structure | Name |
|---|---|---|
| 1 | 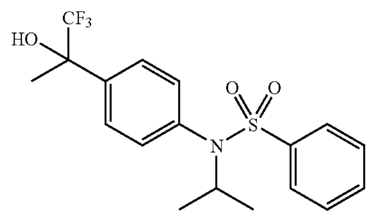 | N-Isopropyl-N-[4-(1,1,1-trifluoro-2-hydroxypropan-2-yl)phenyl]benzenesulfonamide |
| 2 | 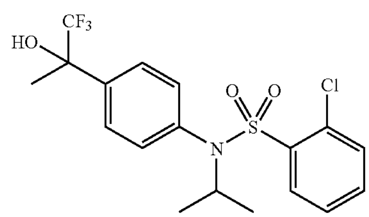 | 2-chloro-N-isopropyl-N-[4-(1,1,1-trifluoro-2-hydroxypropan-2-yl)phenyl]benzenesulfonamide |
| 2a | 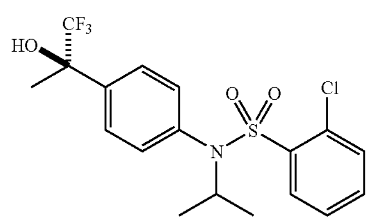 | (R)-2-chloro-N-isopropyl-N-[4-(1,1,1-trifluoro-2-hydroxypropan-2-yl)phenyl]benzenesulfonamide |
| 2b | 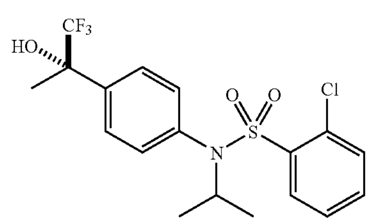 | (S)-2-chloro-N-isopropyl-N-[4-(1,1,1-trifluoro-2-hydroxypropan-2-yl)phenyl]benzenesulfonamide |
| 3 | 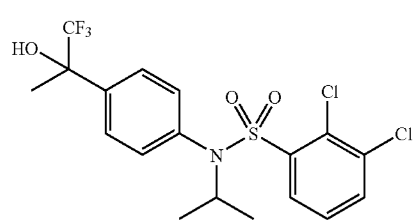 | 2,3-dichloro-N-isopropyl-N-[4-(1,1,1-trifluoro-2-hydroxypropan-2-yl)phenyl]benzenesulfonamide |

| Example | Structure | Name |
| --- | --- | --- |
| 3a | 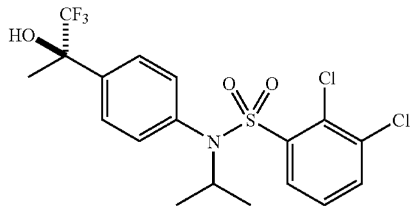 | (R)-2,3-dichloro-N-isopropyl-N-[4-(1,1,1-trifluoro-2-hydroxypropan-2-yl)phenyl]benzenesulfonamide |
| 3b | 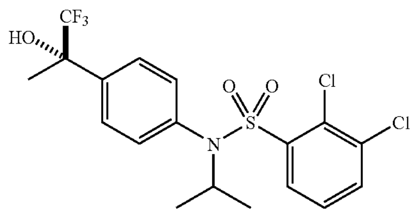 | (S)-2,3-dichloro-N-isopropyl-N-[4-(1,1,1-trifluoro-2-hydroxypropan-2-yl)phenyl]benzenesulfonamide |
| 4 | 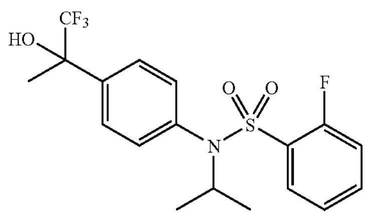 | 2-fluoro-N-isopropyl-N-[4-(1,1,1-trifluoro-2-hydroxypropan-2-yl)phenyl]benzenesulfonamide |
| 5 | 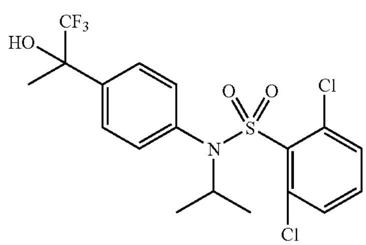 | 2,6-dichloro-N-isopropyl-N-[4-(1,1,1-trifluoro-2-hydroxypropan-2-yl)phenyl]benzenesulfonamide |
| 6 | 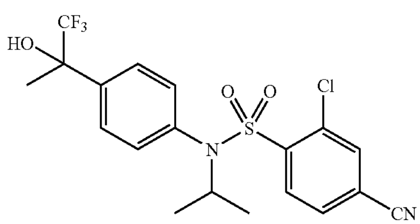 | 2-chloro-4-cyano-N-isopropyl-N-[4-(1,1,1-trifluoro-2-hydroxypropan-2-yl)phenyl]benzenesulfonamide |
| 7 | 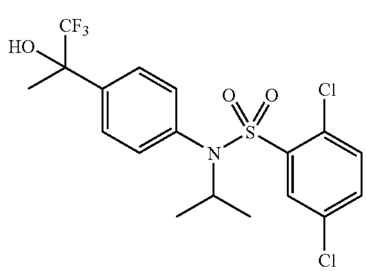 | 2,5-dichloro-N-isopropyl-N-[4-(1,1,1-trifluoro-2-hydroxypropan-2-yl)phenyl]benzenesulfonamide |

-continued

| Example | Structure | Name |
|---|---|---|
| 7a | 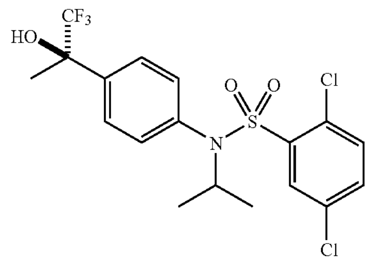 | (R)-2,5-dichloro-N-isopropyl-N-[4-(1,1,1-trifluoro-2-hydroxypropan-2-yl)phenyl]benzenesulfonamide |
| 7b | 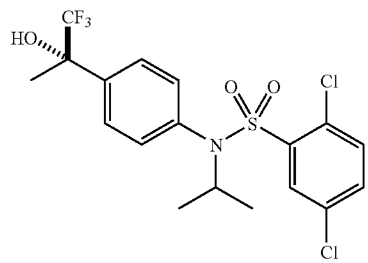 | (S)-2,5-dichloro-N-isopropyl-N-[4-(1,1,1-trifluoro-2-hydroxypropan-2-yl)phenyl]benzenesulfonamide |
| 8 | 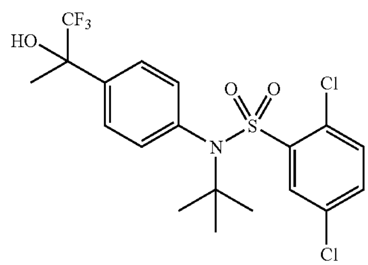 | N-tert-butyl-2,5-dichloro-N-[4-(1,1,1-trifluoro-2-hydroxypropan-2-yl)phenyl]benzenesulfonamide |
| 9 | 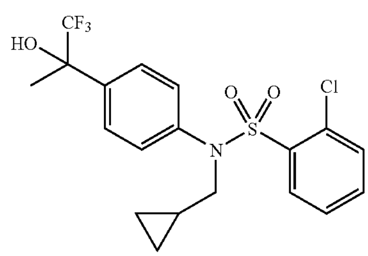 | 2-chloro-N-(cyclopropylmethyl)-N-[4-(1,1,1-trifluoro-2-hydroxypropan-2-yl)phenyl]benzenesulfonamide |
| 10 | 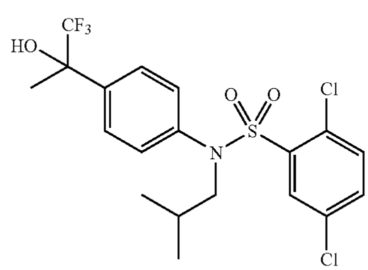 | 2,5-dichloro-N-isobutyl-N-[4-(1,1,1-trifluoro-2-hydroxypropan-2-yl)phenyl]benzenesulfonamide |
| 11 | 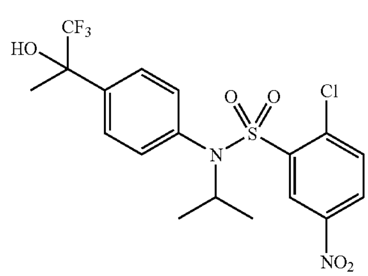 | 2-chloro-N-isopropyl-5-nitro-N-[4-(1,1,1-trifluoro-2-hydroxypropan-2-yl)phenyl]benzenesulfonamide |

-continued

| Example | Structure | Name |
|---|---|---|
| 12 | 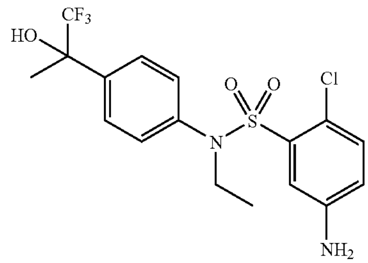 | 5-amino-2-chloro-N-isopropyl-N-[4-(1,1,1-trifluoro-2-hydroxypropan-2-yl)phenyl]benzenesulfonamide |
| 13 | 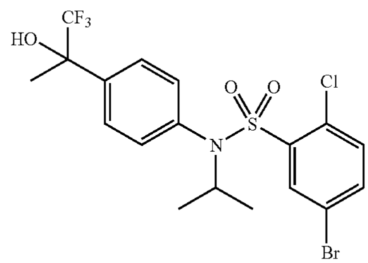 | 5-bromo-2-chloro-N-isopropyl-N-[4-(1,1,1-trifluoro-2-hydroxypropan-2-yl)phenyl]benzenesulfonamide |
| 14 | 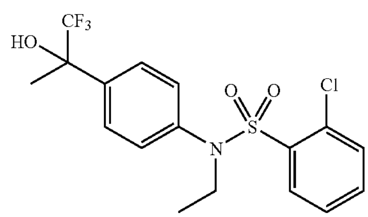 | chloro-N-ethyl-N-[4-(1,1,1-trifluoro-2-hydroxypropan-2-yl)phenyl]benzenesulfonamide |
| 15 | 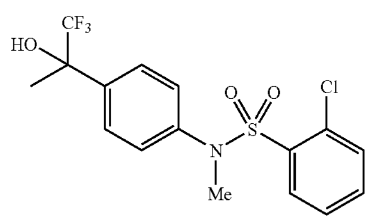 | 2-chloro-N-methyl-N-[4-(1,1,1-trifluoro-2-hydroxypropan-2-yl)phenyl]benzenesulfonamide |
| 16 | 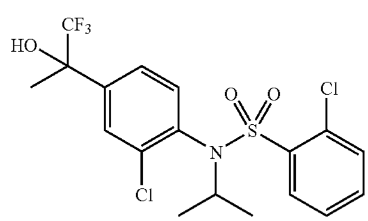 | 2-chloro-N-(2-chloro-4-(1,1,1-trifluoro-2-hydroxypropan-2-yl)phenyl)-N-isopropylbenzenesulfonamide |
| 17 | 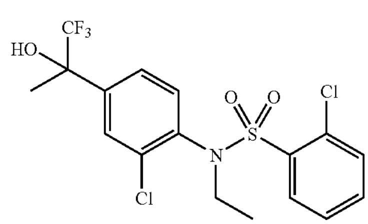 | 2-chloro-N-(2-chloro-4-(1,1,1-trifluoro-2-hydroxypropan-2-yl)phenyl)-N-ethylbenzenesulfonamide |

-continued

| Example | Structure | Name |
|---|---|---|
| 18 | 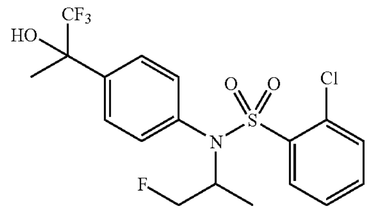 | 2-chloro-N-(1-fluoropropan-2-yl)-N-(4-(1,1,1-trifluoro-2-hydroxypropan-2-yl)phenyl)benzenesulfonamide |
| 19 | 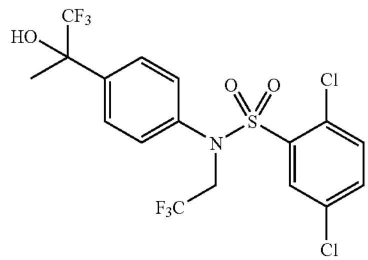 | 2,5-dichloro-N-(2,2,2-trifluoroethyl)-N-[4-(1,1,1-trifluoro-2-hydroxypropan-2-yl)phenyl]benzenesulfonamide |
| 20 | 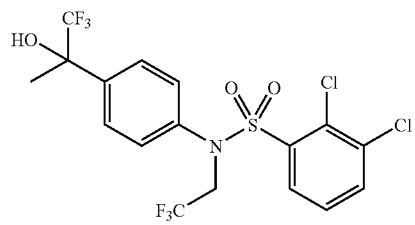 | 2,3-dichloro-N-(2,2,2-trifluoroethyl)-N-[4-(1,1,1-trifluoro-2-hydroxypropan-2-yl)phenyl]benzenesulfonamide |
| 21 | 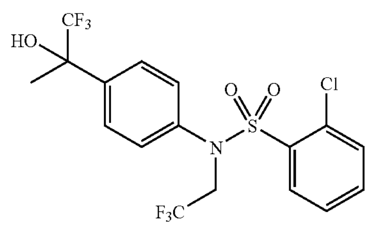 | 2-chloro-N-(2,2,2-trifluoroethyl)-N-[4-(1,1,1-trifluoro-2-hydroxypropan-2-yl)phenyl]benzenesulfonamide |
| 22 | 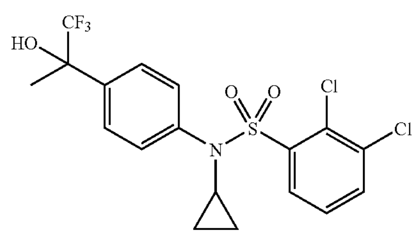 | 2,3-dichloro-N-cyclopropyl-N-[4-(1,1,1-trifluoro-2-hydroxypropan-2-yl)phenyl]benzenesulfonamide |
| 23 | 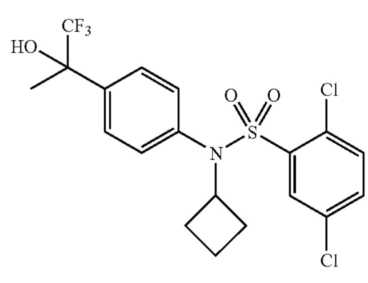 | 2,5-dichloro-N-cyclobutyl-N-[4-(1,1,1-trifluoro-2-hydroxypropan-2-yl)phenyl]benzenesulfonamide |

| Example | Structure | Name |
|---|---|---|
| 24 | 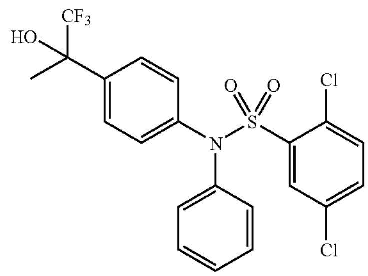 | 2,5-dichloro-N-phenyl-N-[4-(1,1,1-trifluoro-2-hydroxypropan-2-yl)phenyl]benzenesulfonamide |
| 25 | 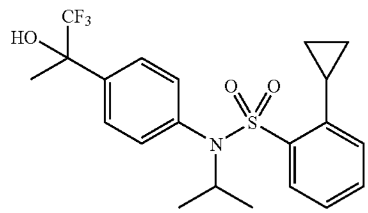 | 2-cyclopropyl-N-isopropyl-N-[4-(1,1,1-trifluoro-2-hydroxypropan-2-yl)phenyl]benzenesulfonamide |

The present invention also provides compositions comprising an aniline sulfonamide derivative of Formula (I) and a pharmaceutically acceptable vehicle, carrier, diluent or excipient.

The invention further provides aniline sulfonamide derivatives of Formula (I) that are in isolated and purified form.

The invention provides methods for treating diabetes comprising administering to a patient in need thereof a therapeutically effective amount of an aniline sulfonamide derivative of Formula (I).

The invention also provides methods for treating obesity comprising administering to a patient in need thereof a therapeutically effective amount of an aniline sulfonamide derivative of Formula (I).

The invention further provides methods for treating an HSD-mediated condition or disorder comprising administering to a patient in need thereof a therapeutically effective amount of an aniline sulfonamide derivative of Formula (I).

The invention further provides methods for treating an 11β-HSD1-mediated condition or disorder comprising administering to a patient in need thereof a therapeutically effective amount of an aniline sulfonamide derivative of Formula (I).

The invention further provides methods for treating an 11β-HSD2-mediated condition or disorder comprising administering to a patient in need thereof a therapeutically effective amount of an aniline sulfonamide derivative of Formula (I).

The invention further provides methods for treating an 17β-HSD3-mediated condition or disorder comprising administering to a patient in need thereof a therapeutically effective amount of an aniline sulfonamide derivative of Formula (I).

The invention further provides methods for treating an HSD-responsive condition or disorder comprising administering to a patient in need thereof a therapeutically effective amount of an aniline sulfonamide derivative of Formula (I).

The invention further provides methods for treating an 11β-HSD1-responsive condition or disorder comprising administering to a patient in need thereof a therapeutically effective amount of an aniline sulfonamide derivative of Formula (I).

The invention further provides methods for treating an 11β-HSD2-responsive condition or disorder comprising administering to a patient in need thereof a therapeutically effective amount of an aniline sulfonamide derivative of Formula (I).

The invention further provides methods for treating an 17β-HSD3-responsive condition or disorder comprising administering to a patient in need thereof a therapeutically effective amount of an aniline sulfonamide derivative of Formula (I).

Preparation of the Aniline Sulfonamide Derivatives of Formula I

Those skilled in the art will recognize that there are a variety of methods available to synthesize molecules represented in the claims. In general, useful methods for synthesizing compounds represented in the claims comprise three parts, which may be done in any order: Formation of a sulfonamide bond, installation of a —$CR^1R^2R^3$ group, and installation or modification of functional groups appended to the —$N(LR^5)SO_2R^6$ group and the $R^4$-substituted aryl ring. Retrosynthetic disconnection of the compounds of the invention into fragments a, b and c, useful for construction of the compounds, is shown below:

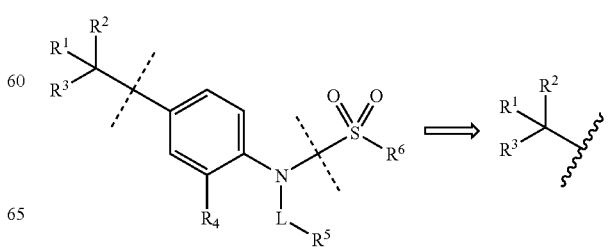

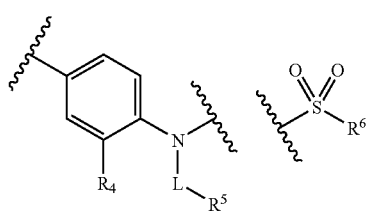

Various methods can be employed to prepare the compounds of this invention (eq. 1-4). Equation one demonstrates one method of forming the sulfonamide linkage. In the case of eq. 1, X may be chosen from an appropriate group such as Cl or F, or from any group capable of activating a sulfonyl group for displacement by an amine (e.g., imidazole, etc.).

eq. 1

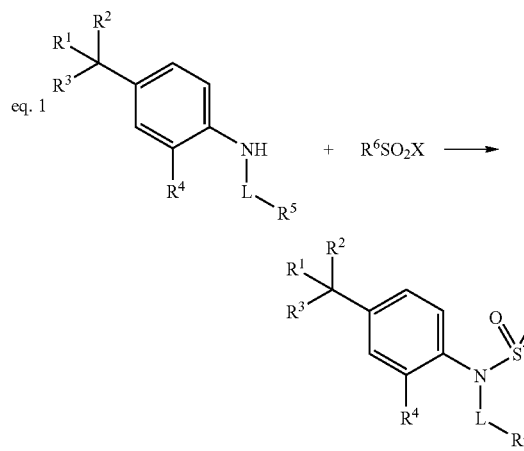

The coupling referred to in eq. 1 can be assisted by the use of organic or inorganic bases, and also by catalysts, such as DMAP and the like. Suitable coupling partners include but are not limited to a sulfonyl chloride and an amine, a sulfonyl fluoride and an amine, $RSO_2$-imidazole and an amine. Those skilled in the art will recognize that there are other possible combinations which will also result in the desired product.

The installation of L-$R^5$ can be accomplished prior to formation of the sulfonamide linkage (eq. 1) or after sulfonamide formation (eq.2). In the latter case, alkylation of the sulfonamide nitrogen can be accomplished using general methods known to those skilled in the art, where X is a halide, triflate, or other group suitable for nucleophilic displacement. The reactions in eq. 2 can be assisted by the use of organic or inorganic bases.

eq. 2

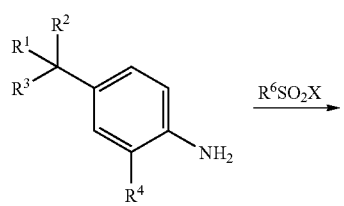

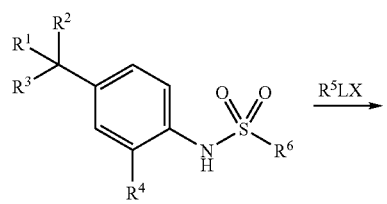

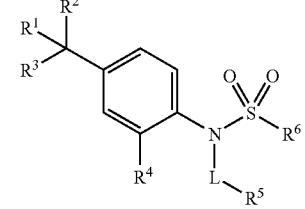

Installation of the —$CR^1R^2R^3$ group can occur before or after the central coupling reaction, and can be further modified at various times during the preparation of the claimed molecules. Equation 3 demonstrates one method in which the —$CR^1R^2R^3$ group is installed in the form of a ketone before the central coupling reaction, followed by further modification to reach compounds of the invention. Following the central coupling, addition of a nucleophile ("Nu") such as $CF_3^-$ or $CH_3^-$ via addition of; e.g., $CF_3TMS$, MeLi, MeMgBr or similar reagent, completes the installation of the —$CR^1R^2R^3$ group. This can be followed by further modification of substituents to complete the preparation.

eq. 3

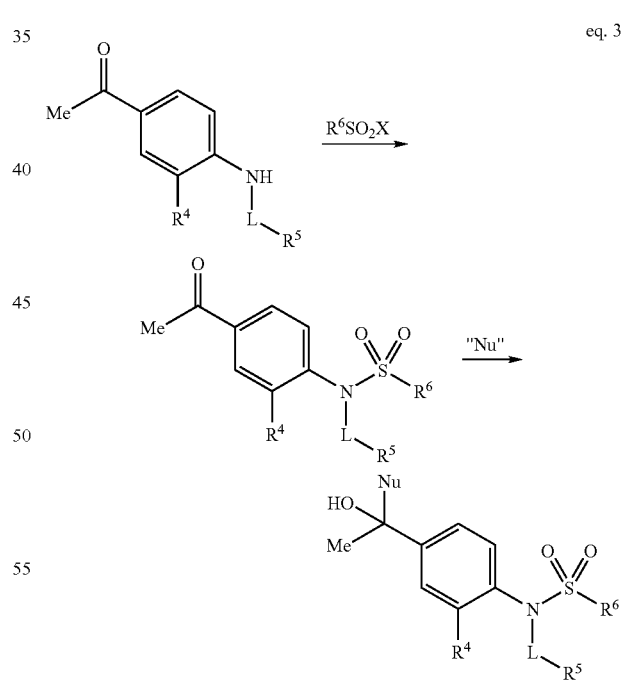

Alternatively, the —$CR^1R^2R^3$ group can be installed following the central coupling via Friedel-Crafts acylation, as shown in eq. 4. Those skilled in the art will understand that this methodology may particularly accommodate some substitution patterns. Further modification as in equations 1, 2, and 3 provides the compounds of the invention.

eq. 4

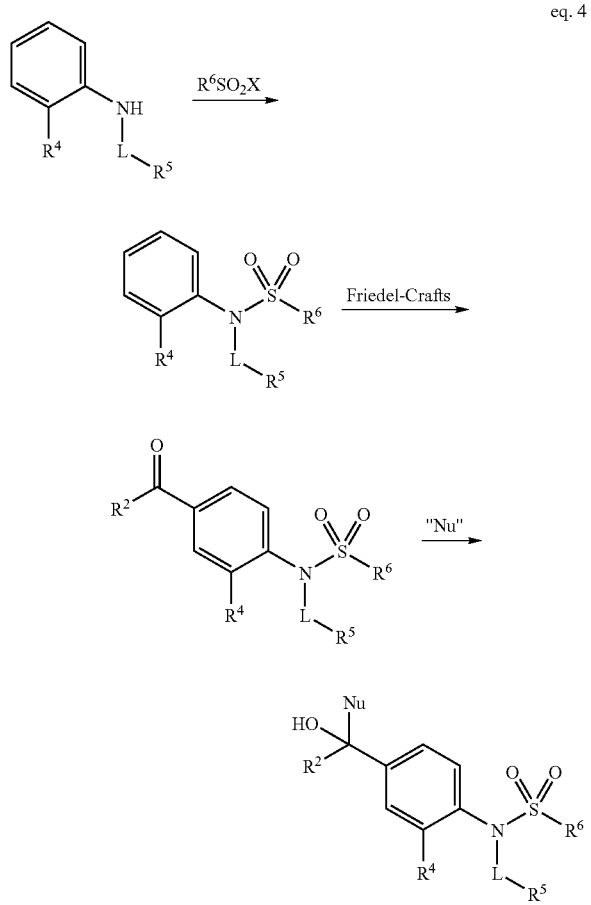

Introduction of the trifluoromethyl carbinol moiety can be achieved via a variety of methods, some of which are exemplified in equations 5-7. The —CF$_3$ group can be introduced by addition to a ketone using CF$_3$TMS and TBAF, or the quaternary ammonium base of TBAF can be substituted with a chiral quaternary base, such as in equation 5, to produce, for example, one enantiomer in excess, such as is described in Caron et al. (2003) *Synthesis* 1693-1698.

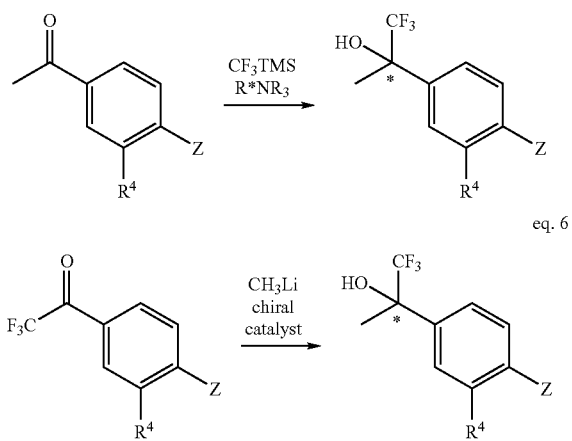

eq. 7

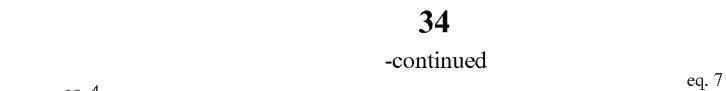
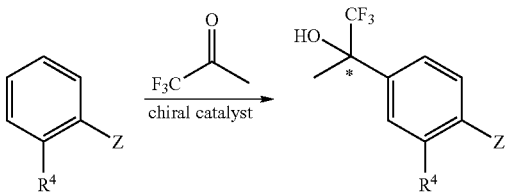

Another useful method is the chiral addition of a nucleophile such as MeLi or MeMgBr mediated via an amine or aminoalcohol additive (eq. 6) to a trifluoromethylketone (for an example, see Thompson et al. (1995) *Tetrahedron Lett.* 49:8937-8940). Yet another useful method is Friedel-Crafts alkylation (eq. 7), which may be done in a fashion to give optically active products using chiral catalysts such as binaphthol derived titanium catalysts (Ishii et al. (2000) *J. Org. Chem.* 65:1597-1599), and chiral copper catalysts (Zhuang et al. (2001) *J. Org. Chem.* 66:1009-1013). One skilled in the art will understand that a variety of methods are available for this transformation. For the most efficient preparation of any particular compound of the invention, one skilled in the art will recognize that the timing of the introduction of the —CR$^1$R$^2$R$^3$ group can vary, and may be the first, last, or intermediate transformation in the preparation of a given compound.

A variety of the methods described above were used to prepare compounds of the invention, some of which are shown in the examples.

Pharmaceutical Compositions

Pharmaceutical compositions and single unit dosage forms comprising an aniline sulfonamide derivative, or a pharmaceutically acceptable stereoisomer, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, effervescent compositions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous (e.g., <1% water) pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The aniline sulfonamide derivatives of formula I can be administered to a mammal (human, horse, mouse, rat, rabbit, dog, cat, bovine, pig, monkey etc.) as an 11β-HSD1 modulator, a prophylactic or therapeutic drug of diabetes, a prophylactic or therapeutic drug of diabetic complication (retinopathy, nephropathy, neuropathy, cardiac infarction and cerebral infarction based on arteriosclerosis etc.), a prophylactic or therapeutic drug of hyperlipemia, a prophylactic or therapeutic drug of obesity, neurodegenerative disease and the like, or a prophylactic or therapeutic drug of diseases mediated by 11β-HSD1.

The aniline sulfonamide derivatives can be administered to a mammal concurrently with an additional therapeutic agent for the treatment of a disease, such as diabetes or obesity, with the aim of the prophylaxis or treatment of a disease. As such, the aniline sulfonamide derivatives of the present invention can be administered in combination with other therapeutic agents for the treatment or prevention of numerous diseases, including, but not limited to, diabetes and obesity.

Depending on the disease to be treated and the patient's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the case of a combined administration, the aniline sulfonamide derivatives may be administered simultaneously with other another therapeutic agent that is useful for the treatment or prevention of diabetes, obesity or other disease or may be administered at a time prior to or subsequent to another therapeutic agent. In the case of combined administration, a pharmaceutical composition containing the aniline sulfonamide derivative and an additional therapeutic agent can be administered. Alternatively, a pharmaceutical composition containing the aniline sulfonamide derivative and a pharmaceutical composition containing an additional therapeutic agent may be administered separately. The administration routes of respective pharmaceutical compositions may be the same or different.

In the case of a combined administration, the aniline sulfonamide derivatives may be administered at a dose of 50 mg to 800 mg per administration, which is given up to several times a day. For example, dosing of once per day or less than once per day is contemplated. In addition, the compound may be administered at a smaller dose. The combined pharmaceutical agent can be administered at a dose generally employed for the prophylaxis or treatment of diabetes or obesity or at a smaller dose than that.

Like the amounts and types of excipients, the amounts and specific types of active ingredients in a dosage form may differ depending on factors such as, but not limited to, the route by which it is to be administered to patients. However, typical dosage forms of the invention comprise an aniline sulfonamide derivative, or a pharmaceutically acceptable salt, solvate, clathrate, hydrate, polymoprh or prodrug thereof. In the treatment or prevention of diabetes, obesity, glaucoma, osteoporosis, cognitive disorders, immune disorders, depression or other conditions or disorders associated with the modulation of an hydroxysteroid dehydrogenase, an appropriate dosage level will generally be from about 0.001 to about 100 mg per kg patient body weight per day which can be administered in single or multiple doses. An exemplary dosage level can be from about 0.01 to about 25 mg/kg per day or about 0.05 to about 10 mg/kg per day. In other embodiments, a suitable dosage level can be from about 0.01 to about 25 mg/kg per day, about 0.05 to about 10 mg/kg per day, or about 0.1 to about 5 mg/kg per day. Within this range the dosage can be from about 0.005 to about 0.05, about 0.05 to about 0.5 or about 0.5 to about 5.0 mg/kg per day lie within the range of from about 0.1 mg to about 2000 mg per day, given as a single once-a-day dose in the morning but typically as divided doses throughout the day taken with food. In one embodiment, the daily dose is administered twice daily in equally divided doses. A daily dose range can be from about 5 mg to about 500 mg per day or between about 10 mg and about 200 mg per day. In managing the patient, the therapy can be initiated at a lower dose, such as from about 1 mg to about 25 mg, and increased if necessary up to from about 200 mg to about 2000 mg per day as either a single dose or divided doses, depending on the patient's global response.

For multidrug therapy, the weight ratio of the compound of the invention to the second active ingredient may be varied and will depend upon the effective dose of each ingredient. Generally, an effective dose of each will be used. Thus, for example, when a compound of the invention is combined with an NSAID, the weight ratio of the compound of the invention to the NSAID will generally range from about 1000:1 to about 1:1000, such as from about 200:1 to about 1:200. Combinations of a compound of the invention and other active ingredients will generally also be within the aforementioned range, but in each case, an effective dose of each active ingredient should be used.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

For oral administration, the compositions can be provided in the form of tablets containing about 1 to about 1000 milligrams of the active ingredient. In other embodiments, the compositions are provided in provided in the form of tablets containing about 1.0, about 5.0, about 10.0, about 15.0, about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, or about 1000.0 milligrams of the active ingredient for the symptomatic adjustment of the dosage to the patient to be treated. The compounds may be administered on a regimen of 1 to 4 times per day, such as once or twice per day.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

Controlled-release pharmaceutical products can improve drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms can be sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. For example, lyophilized sterile compositions suitable for reconstitution into particulate-free dosage forms suitable for administration to humans.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

In some embodiments, parenteral dosage forms used for the methods of preventing, treating or managing disease in a cancer patient.

Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants also can be added to pharmaceutical compositions and dosage forms if desired. Examples of such additional ingredients are well known in the art. See, e.g., Remington's Pharmaceutical Sciences, 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Mucosal Dosage Forms and Lung Delivery

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of the invention can also be administered directly to the lung by inhalation (see e.g., Tong et al., International Publication. No. WO 97/39745; Clark et al, International Publication No. WO 99/47196, which are herein incorporated by reference). For administration by inhalation, an aniline sulfonamide derivative can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver an aniline sulfonamide derivative directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer an aniline sulfonamide derivative to the lung (See, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver an aniline sulfonamide derivative to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver an aniline sulfonamide derivative to the lung. Nebulizers create aerosols from liquid drug formulations by using, for example, ultrasonic energy to form fine particles that can be readily inhaled (See e.g., Verschoyle et al., British J Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics. Inhaled compounds, delivered by nebulizer devices, are currently under investigation as treatments for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In another embodiment, an electrohydrodynamic ("EHD") aerosol device is used to deliver an aniline sulfonamide derivative to the lung. EHD aerosol devices use electrical energy to aerosolize liquid drug solutions or suspensions (see e.g., Noakes et al., U.S. Pat. No. 4,765,539; Coffee, U.S. Pat. No., 4,962,885; Coffee, International Publication No. WO 94/12285; Coffee, International Publication No. WO 94/14543; Coffee, International Publication No. WO 95/26234, Coffee, International Publication No. WO 95/26235, Coffee, International Publication No. WO 95/32807, which are herein incorporated by reference). The electrochemical properties of the compound of the invention formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of an aniline sulfonamide derivative will be known to the skilled artisan and are within the scope of the invention.

Liquid drug formulations suitable for use with nebulizers and liquid spray devices and EHD aerosol devices will typically include an aniline sulfonamide derivative with a pharmaceutically acceptable carrier. In some embodiments, the pharmaceutically acceptable carrier is a liquid such as alcohol, water, polyethylene glycol or a perfluorocarbon. Optionally, another material may be added to alter the aerosol properties of the solution or suspension of an aniline sulfonamide derivative. This material can be a liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference). A compound of the invention can also be formulated in rectal or vaginal compositions such as suppositories or retention enemas, e.g., containing conventional suppository bases such as cocoa butter or other glycerides.

In addition to the formulations described previously, an aniline sulfonamide derivative can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other Delivery Systems

Alternatively, other pharmaceutical delivery systems can be employed. Liposomes and emulsions are well known examples of delivery vehicles that can be used to deliver an aniline sulfonamide derivative. Certain organic solvents such as dimethylsulfoxide can also be employed, although usually at the cost of greater toxicity. A compound of the invention can also be delivered in a controlled release system. In one embodiment, a pump can be used (Sefton, CRC Crit. Ref Biomed Eng., 1987, 14, 201; Buchwald et al., Surgery, 1980, 88, 507; Saudek et al., N. Engl. J Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J Macromol. Sci. Rev. Macromol. Chem., 1983, 23, 61; see also Levy et al., Science 1985, 228, 190; During et al., Ann. Neurol., 1989,25,351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g., Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Therapeutic Uses Of The Aniline Sulfonamide Derivatives

In one aspect, the invention provides methods of treating or preventing a condition or disorder associated with the modulation of hydroxysteroid dehydrogenases by administering to a patient having such a condition or disorder a therapeutically effective amount of a compound or composition of the invention. In one group of embodiments, conditions and disorders, including chronic diseases of humans or other species, can be treated with modulators, stimulators, or inhibitors of hydroxysteroid dehydrogenases, such as 11β-HSD1.

Treatment or Prevention of Diabetes

Diabetes and diabetic conditions can be treated or prevented by administration of a therapeutically effective amount of an aniline sulfonamide derivative.

Types of diabetes that can be treated or prevented by administering a therapeutically effective amount of an aniline sulfonamide derivative include type I diabetes mellitus juvenile onset diabetes, insulin dependent-diabetes mellitus or IDDM), type II diabetes mellitus (non-insulin-dependent diabetes mellitus or NIDDM), insulinopathies, diabetes associated with pancreatic disorders, diabetes associated with other disorders (such as Cushing's Syndrome, acromegaly, pheochromocytoma, glucagonoma, primary aldosteronism, and somatostatinoma), type A and type B insulin resistance syndromes, lipatrophic diabetes, and diabetes induced by β-cell toxins.

In some embodiments, the type of diabetes being treated is type II diabetes.

Treatment or Prevention of Obesity

Obesity can be treated or prevented by administration of a therapeutically effective amount of an aniline sulfonamide derivative.

Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Metabolic disorders, such as hyperlidemia and diabetes, and cardiovascular disorders, such as hypertension and coronary artery disease, are commonly associated with obesity.

Complications due to obesity may also be treated or prevented by administering a therapeutically effective amount of an aniline sulfonamide derivative. Such complications include, but are not limited to, sleep apnea, Pickwickian syndrome, orthopedic disturbances of weight-bearing and non-weight-bearing joints, and skin disorders resulting from increased sweat or skin secretions.

Treatment or Prevention of Other Conditions

Other conditions that can be treated or prevented by administering a therapeutically effective amount of an aniline sulfonamide derivative include, but are not limited to any condition which is responsive to the modulation, such as inhibition, of hydroxysteroid dehydrogenases or specific isoforms thereof, and thereby benefit from administration of such a modulator. Representative conditions in this regard include, but are not limited to, metabolic disorders and related cardiovascular risk factors such as syndrome X, polycystic ovarian disease, eating disorders (e.g., anorexia and bulimia), craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia and Cushing's syndrome; diseases associated therewith such as hypertension, atherosclerosis, vascular restenosis, retinopathy and nephropathy; neurologic disorders such as neurodegenerative disease, neuropathy and muscle wasting; cognitive disorders, such as age-related learning disorders, dementia, neurodegeneration, as well as for improvement of cognitive function in subjects ranging from the severely impaired (e.g., Parkinsons's or Alzheimer's associated dementia) to mildly impaired (e.g., age-associated memory impairment, drug-induced cognitive impairment) to unimpaired subjects (e.g., cognitive enhancers for the general population) (see, Sandeep, et al., PNAS, electronically available at www.pnas.org/cgi/doi/10.1073/pnas.0306996101); androgen and/or estrogen-related disorders such as prostate cancer, colon cancer, breast cancer, benign prostatic hyperplasia, ovarian cancer, uterine cancer, and male pseudohermaphrodism; endometriosis, dementia, depression, psoriasis, glaucoma, osteoporosis, viral infections, inflammatory disorders, and immune disorders.

Additional Therapeutic Agents

In one embodiment, the present methods for treating or preventing further comprise the administration of a therapeutically effective amount of another therapeutic agent useful for treating or preventing the diseases or disorders disclosed herein. In this embodiment, the time in which the therapeutic effect of the other therapeutic agent is exerted overlaps with the time in which the therapeutic effect of the aniline sulfonamide derivative is exerted.

The compounds of the invention can be combined or used in combination with other agents useful in the treatment, prevention, suppression or amelioration of the conditions or disorders for which compounds of the invention are useful, including diabetes, obesity, glaucoma, osteoporosis, cognitive disorders, immune disorders, depression and those pathologies noted above.

Such other agents, or drugs, can be administered, by a route and in an amount commonly used therefor, simultaneously or sequentially with an aniline sulfonamide derivative. In one embodiment, a pharmaceutical composition contains such other drugs in addition to the compound of the invention when an aniline sulfonamide derivative is used contemporaneously with one or more other drugs. Accordingly, the pharmaceutical compositions of the invention include those that also contain one or more other active ingredients or therapeutic agents, in addition to an aniline sulfonamide derivative.

In one embodiment, for the treatment or prevention of diabetes, an aniline sulfonamide derivative can be administered with another therapeutic agent, including, but not limited to, anti-diabetic agents such as insulin, inhaled insulin (Exubera®), insulin mimetics, insulin secretogues, sulfonylureas (e.g., glyburide, meglinatide, glimepiride, gliclazide, glipizide, gliquidone, chloropropresponsivemide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide), biguanides (e.g., metformin (Glucophage®)), α-glucosidase inhibitors (e.g., acarbose, voglibose and miglitol), thiazolidinone compounds (e.g., rosiglitazone (Avandia®), troglitazone (Rezulin®), ciglitazone, pioglitazone (Actos®) and englitazone), prandial glucose regulators (e.g., repaglinide and nateglinide) and glucagon receptor antagonists.

In another embodiment, for the treatment or prevention of obesity, an aniline sulfonamide derivative can be administered with another therapeutic agent, including, but not limited to, β3 adrenergic receptor agonists, leptin or derivatives thereof, neuropeptide Y (e.g., NPY5) antagonists, and mazindol.

Examples of other therapeutic agents that may be combined with an aniline sulfonamide derivative, either administered separately or in the same pharmaceutical compositions, include, but are not limited to: (i) cholesterol lowering agents such as HMG-CoA reductase inhibitors (e.g., lovastatin, simvastatin (Zocor®), pravastatin, fluvastatin, atorvastatin (Lipitor®) and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (ii) antithrombotic agents, such as thrombolytic agents (e.g., streptokinase, alteplase, anistreplase and reteplase), heparin, hirudin and warfarin derivatives, β-blockers (e.g., atenolol), β adrenergic agonists (e.g., isoproterenol), angiotensin II antagonists, ACE inhibitors and vasodilators (e.g., sodium nitroprusside, nicardipine hydrochloride, nitroglycerin and enaloprilat); (iii) PPAR agonists, e.g., PPARγ and PPARδ agonists; (iv) DP antagonists; (v) lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin; (vi) glaucoma therapies such as cholinergic agonists (e.g., pilocarpine and carbachol), cholinesterase inhibitors (e.g., physostigmine, neostigmine, demacarium, echothiophate iodide and isofluorophate), carbonic anhydrase inhibitors (e.g., acetazolamide, dichlorphenamide, methazolamide, ethoxzolamide and dorzolamide), non-selective adrenergic agonists (e.g., epinephrine and dipivefrin), $\alpha_2$-selecteive adrenergic agonists (e.g., apraclonidine and brimonidine), β-blockers (e.g., timolol, betazolol, levobunolol, carteolol and metipranolol), prostaglandin analogs (e.g., latanoprost) and osmotic diuretics (e.g., glycerin, mannitol and isosorbide); corticosteroids, such as beclomethasone, methylprednisolone, betamethasone, prednisone, prenisolone, dexamethasone, fluticasone and hydrocortisone, and corticosteroid analogs such as budesonide; (vii) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (viii) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetylsalicylic acid and sulfasalazine) and the pyrazolones (e.g., apazone, bezpiperylon, feprazone, mofebutazone, oxyphenbutazone and phenylbutazone); (ix) cyclooxygenase-2 (COX-2) inhibitors such as celecoxib (Celebrex®) and rofecoxib (Vioxx®); (xi) inhibitors of phosphodiesterase type IV (PDE-IV); (xii) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (xiii) a hepatoprotective agent; and (xiv) other compounds such as 5-aminosalicylic acid and prodrugs thereof.

The weight ratio of the compound of the invention to the second active ingredient may be varied and will depend upon the effective dose of each ingredient. Generally, an effective dose of each will be used. Thus, for example, when an aniline sulfonamide derivative is combined with an NSAID, the weight ratio of the compound of the invention to the NSAID will generally range from about 1000:1 to about 1:1000, such as about 200:1 to about 1:200. Combinations of an aniline sulfonamide derivative and other active ingredients will generally also be within the aforementioned range, but in each case, an effective dose of each active ingredient should be used.

Kits

The invention encompasses kits that can simplify the administration of the aniline sulfonamide derivatives or composition of the invention to a patient.

A typical kit of the invention comprises a unit dosage of an aniline sulfonamide derivative. In one embodiment, the unit dosage form is in a container, which can be sterile, containing a therapeutically effective amount of an aniline sulfonamide derivative and a pharmaceutically acceptable vehicle. In another embodiment, the unit dosage form is in a container containing a therapeutically effective amount of an aniline sulfonamide derivative as a lyophilate or pharmaceutically acceptable salt. In this instance, the kit can further comprise another container that contains a solution useful for the reconstitution of the lyophilate or dissolution of the salt. The kit can also comprise a label or printed instructions for use of the aniline sulfonamide derivatives.

The kits fo the instant invention may also comprise a second therapeutic agent that can be administered sequentially, separately, or concomitantly. Non-limiting examples of such second therapeutic agents are described hereinabove.

In a further embodiment, the kit comprises a unit dosage form of a composition of the invention.

Kits of the invention can further comprise one or more devices that are useful for administering the unit dosage forms of the aniline sulfonamide derivatives or a composition of the invention. Examples of such devices include, but are not limited to, a syringe, a drip bag, a patch or an enema, which optionally contain the unit dosage forms.

*****

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence.

EXAMPLES

The aniline sulfonamide derivatives represented by the formulas of the present invention and the methods of making thereof are explained in detail in the following Examples, which are not to be construed as limiting the invention.

Example 1

Preparation of N-isopropyl-N-[4-(1,1,1-trifluoro-2-hydroxypropan-2-yl)phenyl]benzenesulfonamide (1)

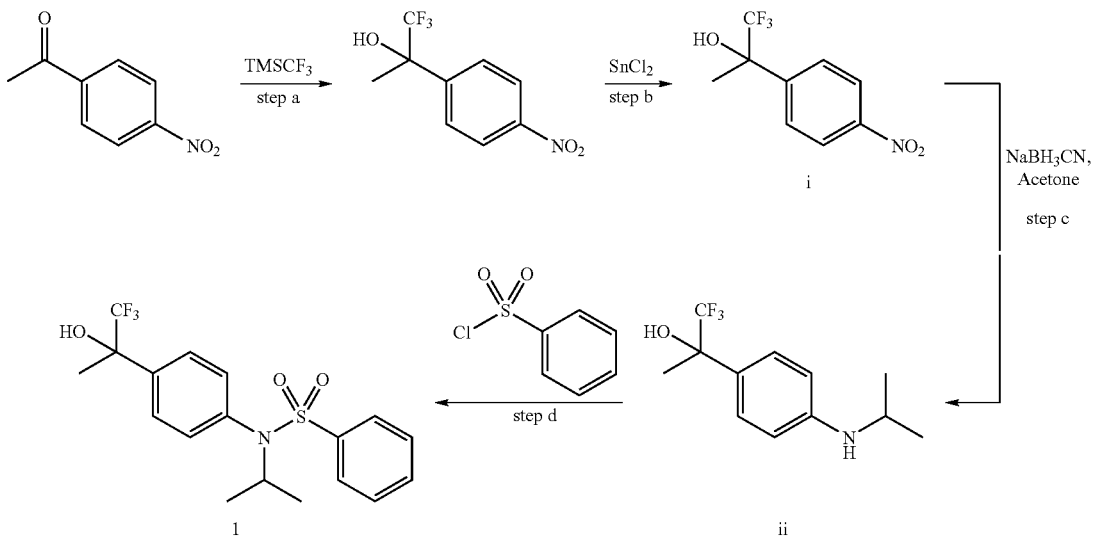

(a) 1,1,1-Trifluoro-2-(4-nitrophenyl)propan-2-ol. A solution of 4'-nitroacetophenone (15.0 g, 90.8 mmol, 1.0 equiv) and TMS-CF$_3$ (39.9 mL, 272 mmol, 3.0 equiv) in THF (150 mL) was treated at 0° C. with tetrabutylammonium fluoride (45.0 mL, 1.0 M in THF, 45.0 mmol, 0.5 equiv). The reaction mixture was stirred for 1 h, diluted (EtOAc), washed (1×H$_2$O and 1×brine), dried (Na$_2$SO$_4$), and concentrated under reduced pressure. Flash chromatography of the residue (SiO$_2$, 20-25% EtOAc/Hexane, gradient elution) provided the product as a yellow solid.

(b) 2-(4-Aminophenyl)-1,1,1-trifluoropropan-2-ol (i). A solution of 1,1,1-trifluoro-2-(4-nitrophenyl)propan-2-ol prepared as in step (a) (19.5 g, 82.9 mmol, 1.0 equiv) in EtOH (300 mL) was treated with SnCl$_2$ (78.6 g, 415 mmol, 5.0 equiv). After stirring at 70° C. for 2 h, the reaction mixture was concentrated under reduced pressure, diluted (EtOAc) and washed (3×1 N aqueous NaOH and 1×brine). The organic extracts were dried (Na$_2$SO$_4$) and concentrated under reduced pressure to provide the product as a yellow solid.

(c) 1,1,1-Trifluoro-2-[4-(isopropylamino)phenyl]propan-2-ol (ii). A solution of 2-(4-aminophenyl)-1,1,1-trifluoropropan-2-ol prepared above in step (b) (8.80 g, 42.9 mmol, 1.0 equiv) and acetone (15.7 mL, 215 mmol, 5.0 equiv) in CH$_3$CN (90 mL) was treated at 0° C. with NaBH$_3$CN (13.5 g, 215 mmol, 5.0 equiv). The reaction was stirred for 10 min at 0° C., treated with AcOH (8.1 mL, 141 mmol, 3.3 equiv) and stirred for 2 h at 25° C. The reaction mixture was treated again with AcOH (8.1 mL, 141 mmol, 3.3 equiv) and stirred for 28 h. The reaction was quenched (1 M aqueous NaOH), extracted (EtOAc), dried ($Na_2SO_4$) and concentrated under reduced pressure. Flash chromatography of the residue ($SiO_2$, 5-10% $MeOH/CH_2Cl_2$ containing 1% of 28% $NH_3$ in $H_2O$, gradient elution) afforded the product as a yellow foam.

(d) N-Isopropyl-N-[4-(1,1,1-trifluoro-2-hydroxypropan-2-yl)phenyl]benzenesulfonamide (1). A solution of 1,1,1-trifluoro-2-[4-(isopropylamino)phenyl]propan-2-ol prepared above in step (c) (40 mg, 0.16 mmol, 1.0 equiv) and benzenesulfonyl chloride (30 mg, 0.16 mmol, 1.0 equiv) in $CH_2Cl_2$ (1.0 mL) was treated with pyridine (39 µL, 0.48 mmol, 3.0 equiv). After stirring at 25° C. for 2 days, the reaction was diluted (EtOAc) and washed (1×1 M aqueous HCl, 1×saturated $NaHCO_3$, and 1×brine). The organics were dried ($Na_2SO_4$) and concentrated under reduced pressure. Flash chromatography of the residue ($SiO_2$, 20% EtOAc/Hexane) gave the product as a pale yellow solid. $^1$H NMR ($CDCl_3$, 500 MHz) δ 7.75 (d, J=8.4 Hz, 2H), 7.56-7.46 (m, 5H), 7.07 (d, J=8.4 Hz, 2H), 4.63-4.57 (m, 1H), 2.37 (s, 1H), 1.79 (s, 3H), 1.05 (d, J=6.7 Hz, 3H), 1.04 (d, J=6.7 Hz, 3H). MS (ESI) 388 [M+H]$^+$.

Example 2

Preparation of 2-chloro-N-isopropyl-N-[4-(1,1,1-trifluoro-2-hydroxypropan-2-yl)phenyl]benzenesulfonamide (2)

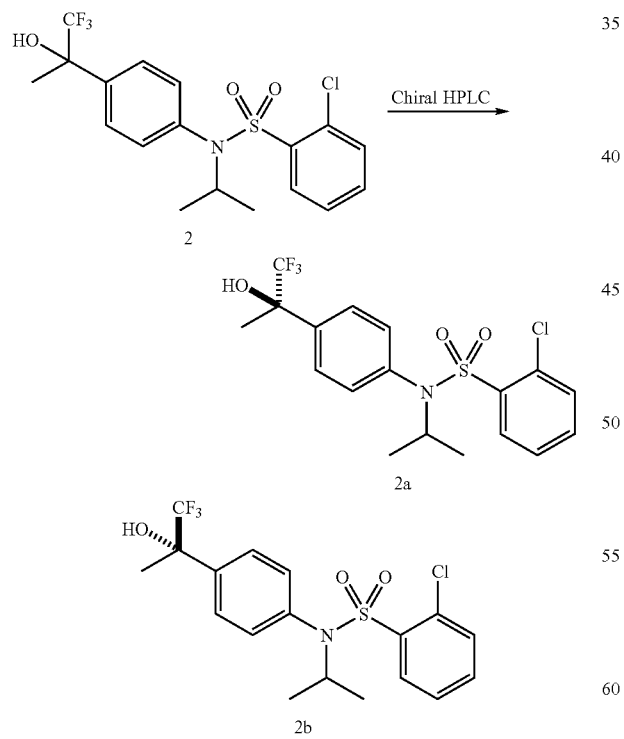

Following steps (a), (b), (c), and (d) described above in Example 1, but substituting 2-chlorobenzenesulfonyl chloride for benzenesulfonyl chloride in step (d), 2-chloro-N-isopropyl-N-[4-(1,1,1-trifluoro-2-hydroxypropan-2-yl)phenyl]benzenesulfonamide (2) was prepared. The racemic product was resolved by chiral HPLC to give optical isomers 2a and 2b. $^1$H NMR ($CDCl_3$, 500 MHz) δ 7.82 (dd, J=1.5, 7.9 Hz, 1H), 7.54-7.43 (m, 4H), 7.25-7.23 (m, 1H) 7.12 (d, J=8.6 Hz, 2H), 4.78-4.70 (m, 1H), 2.36 (s, 1H), 1.75 (s, 3H), 1.16 (d, J=6.7 Hz, 3H), 1.15 (d, J=6.7 Hz, 3H). MS (ESI) 422 [M+H]$^+$. The flow rate was 18 mL/min on a Chiralpak AD-H 20 mm I.D.×250 mm, 5 mic column (Daicel Chemical Industries LTD), using 5% isopropyl alcohol/hexane as the eluent. Complete resolution was achieved at up to 30 mg racemate per injection.

Example 3

Preparation of 2,3-dichloro-N-isopropyl-N-[4-(1,1,1-trifluoro-2-hydroxypropan-2-yl)phenyl]benzenesulfonamide (3)

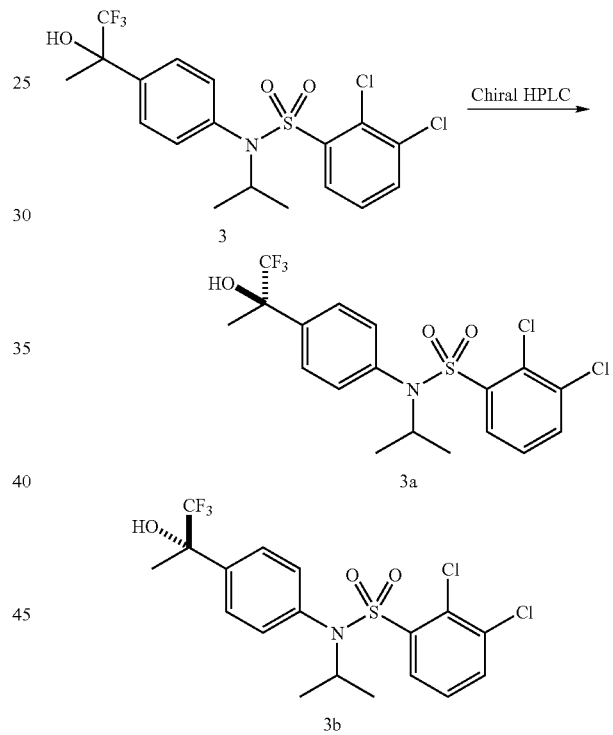

Following steps (a), (b), (c), and (d) described above in Example 1, but substituting 2,3-dichlorobenzenesulfonyl chloride for benzenesulfonyl chloride in step (d), 2,3-dichloro-N-isopropyl-N-[4-(1,1,1-trifluoro-2-hydroxypropan-2-yl)phenyl]benzenesulfonamide (3) was prepared. The racemic product was resolved by chiral HPLC to give optical isomers 3a and 3b. $^1$H NMR ($CDCl_3$, 500 MHz) δ 7.76 (dd, J=1.4, 8.0 Hz, 1H), 7.62 (dd, J=1.4, 8.0 Hz, 1H), 7.50 (d, J=8.5 Hz, 2H), 7.18 (dd, J=8.0, 8.0 Hz, 1H), 7.10 (d, J=8.5 Hz, 2H), 4.79-4.73 (m, 1H), 2.35 (s, 1H), 1.76 (s, 3H), 1.17 (d, J=6.7 Hz, 3H), 1.16 (d, J=6.7 Hz, 3H). MS (ESI) 456 [M+H]$^+$. The flow rate was 10 mL/min on a Chiralpak AS-H 20 mm I.D.×250 mm, 5 mic column (Daicel Chemical Industries LTD), using 10% isopropyl alcohol/hexane as the eluent. Complete resolution was achieved at up to 30 mg racemate per injection.

Example 4

Preparation of 2-fluoro-N-isopropyl-N-[4-(1,1,1-trifluoro-2-hydroxypropan-2-yl)phenyl]benzenesulfonamide (4)

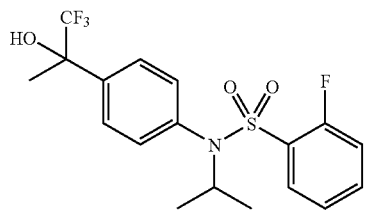

Following steps (a), (b), (c), and (d) described above in Example 1, but substituting 2-fluorobenzenesulfonyl chloride for benzenesulfonyl chloride in step (d), 2-fluoro-N-isopropyl-N-[4-(1,1,1-trifluoro-2-hydroxypropan-2-yl)phenyl]benzenesulfonamide (4) was prepared. $^1$H NMR (CDCl$_3$, 500 MHz) δ 7.75-7.71 (m, 1H), 7.59-7.55 (m, 1H), 7.55 (d, J=8.5 Hz, 2H), 7.27-7.19 (m, 2H), 7.12 (d, J=8.5 Hz, 2H), 4.78-4.72 (m, 1H), 2.40 (s, 1H), 1.80 (s, 3H), 1.16 (d, J=6.7 Hz, 3H), 1.15 (d, J=6.7 Hz, 3H). MS (ESI) 406 [M+H]$^+$.

Example 5

Preparation of 2,6-dichloro-N-isopropyl-N-[4-(1,1,1-trifluoro-2-hydroxypropan-2-yl)phenyl]benzenesulfonamide (5)

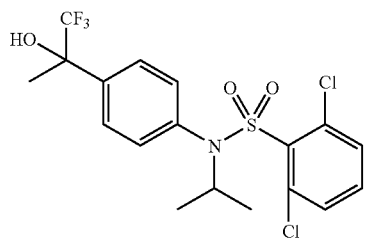

Following steps (a), (b), (c), and (d) described above in Example 1, but substituting 2,6-dichlorobenzenesulfonyl chloride for benzenesulfonyl chloride in step (d), 2,6-dichloro-N-isopropyl-N-[4-(1,1,1-trifluoro-2-hydroxypropan-2-yl)phenyl]benzenesulfonamide (5) was prepared. $^1$H NMR (CDCl$_3$, 400 MHz) δ 7.52 (d, J=8.4 Hz, 2H), 7.39-7.36 (m, 2H), 7.29-7.26 (m, 1H), 7.15 (d, J=8.4 Hz, 2H), 4.85-4.78 (m, 1H), 2.37 (s, 1H), 1.77 (s, 3H), 1.18 (d, J=6.7 Hz, 3H), 1.17 (d, J=6.7 Hz, 3H). MS (ESI) 456 [M+H]$^+$.

Example 6

Preparation of 2-chloro-4-cyano-N-isopropyl-N-[4-(1,1,1-trifluoro-2-hydroxypropan-2-yl)phenyl]benzenesulfonamide (6)

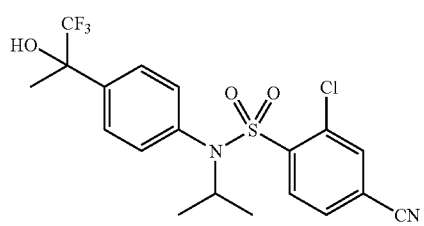

Following steps (a), (b), (c), and (d) described above in Example 1, but substituting 2-chloro-4-cyanobenzenesulfonyl chloride for benzenesulfonyl chloride in step (d), 2-chloro-4-cyano-N-isopropyl-N-[4-(1,1,1-trifluoro-2-hydroxypropan-2-yl)phenyl]benzenesulfonamide (6) was prepared. $^1$H NMR (CDCl$_3$, 500 MHz) δ 7.91 (d, J=8.2 Hz, 1H), 7.83 (d, J=1.4 Hz, 1H), 7.53 (dd, J=1.4, 8.2 Hz, 1H), 7.52 (d, J=8.4 Hz, 2H) 7.05 (d, J=8.4 Hz, 2H), 4.83-4.76 (m, 1H), 2.36 (s, 1H), 1.77 (s, 3H), 1.18 (d, J=6.7 Hz, 3H), 1.17 (d, J=6.7 Hz, 3H). MS (ESI) 447 [M+H]$^+$.

Example 7

Preparation of 2,5-dichloro-N-isopropyl-N-[4-(1,1,1-trifluoro-2-hydroxypropan-2-yl)phenyl]benzenesulfonamide (7)

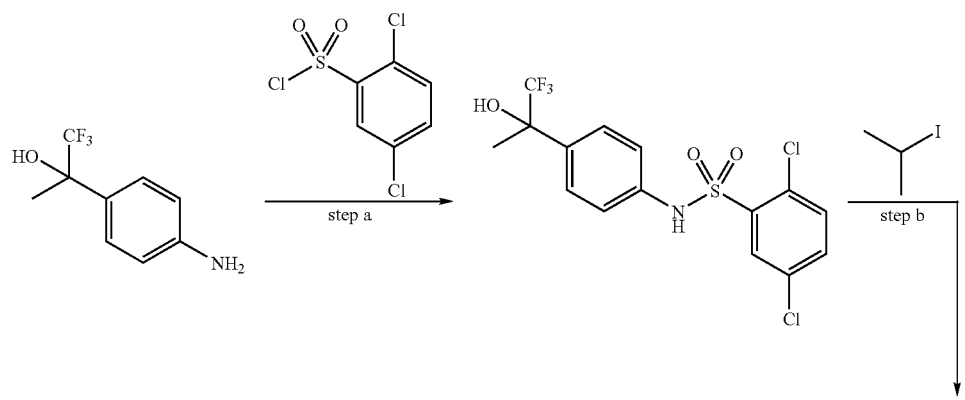

-continued

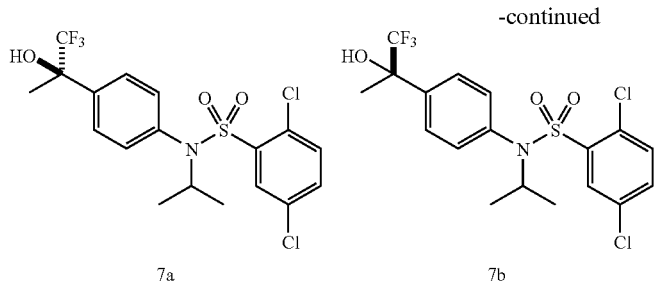

7a   7b

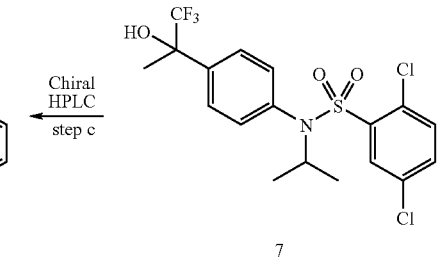

Chiral HPLC step c

7

(a) 2,5-Dichloro-N-[4-(1,1,1-trifluoro-2-hydroxypropan-2-yl)phenyl]benzenesulfonamide. A solution of 2-(4-aminophenyl)-1,1,1-trifluoropropan-2-ol (i) prepared above in step (b) in Example 1 (1.00 g, 4.87 mmol, 1.0 equiv) and 2,5-dichlorobenzenesulfonyl chloride (1.21 g, 4.87 mmol, 1.0 equiv) in $CH_2Cl_2$ (20 mL) was treated with pyridine (1.18 mL, 14.6 mmol, 3.0 equiv). After stirring for 1.5 h, the solution was diluted (EtOAc) and washed (1×1 M aqueous HCl, 1×saturated aqueous $NaHCO_3$, and 1×brine). The organics were dried ($Na_2SO_4$) and concentrated under reduced pressure. Flash chromatography of the residue ($SiO_2$, 30% EtOAc/Hexane) gave the product as a yellow solid.

(b) 2,5-Dichloro-N-isopropyl-N-[4-(1,1,1-trifluoro-2-hydroxypropan-2-yl)phenyl]benzenesulfonamide (7). A solution of 2,5-dichloro-N-[4-(1,1,1-trifluoro-2-hydroxypropan-2-yl)phenyl]benzenesulfonamide prepared above in step (a) (103 mg, 0.25 mmol, 1.0 equiv.) in DMF (2.0 mL) was treated with isopropyl iodide (250 μL, 2.50 mmol, 10 equiv.) and $K_2CO_3$ (346 mg, 2.50 mmol, 10 equiv). After stirring at 75° C. for 1 h, the solution was diluted (EtOAc) and washed (3×brine). The organics were dried ($Na_2SO_4$) and concentrated under reduced pressure. Flash chromatography of the residue ($SiO_2$, 25% EtOAc/Hexane) gave the product 7 as a pale yellow solid.

(c) The racemic product was resolved by chiral HPLC to give optical isomers 7a and 7b. $^1$H NMR ($CDCl_3$, 400 MHz) δ 7.82 (d, J=2.4 Hz, 1H), 7.52 (d, J=8.4 Hz, 2H), 7.48-7.39 (m, 2H), 7.11 (d, J=8.4 Hz, 2H), 4.75-4.68 (m, 1H), 2.37 (s, 1H), 1.77 (s, 3H), 1.16 (d, J=6.7 Hz, 3H), 1.15 (d, J=6.7 Hz, 3H). MS (ESI) 456 [M+H]$^+$. The flow rate was 18 mL/min on a Chiralpak AS-H 20 mm I.D.×250 mm, 5 mic column (Daicel Chemical Industries LTD), using 7% isopropyl alcohol/hexane as the eluent. Complete resolution was achieved at up to 30 mg racemate per injection

Example 8

Preparation of N-tert-butyl-2,5-dichloro-N-[4-(1,1,1-trifluoro-2-hydroxypropan-2-yl)phenyl]benzenesulfonamide (8)

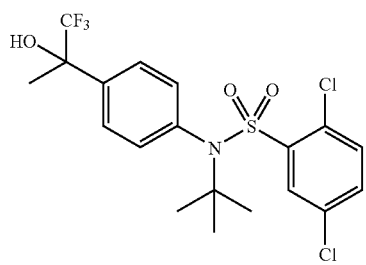

8

Following step (b) described above in Example 7, but substituting tert-butyl bromide for isopropyl iodide, N-tert-butyl-2,5-dichloro-N-[4-(1,1,1-trifluoro-2-hydroxypropan-2-yl)phenyl]benzenesulfonamide (8) was prepared. $^1$H NMR ($CDCl_3$, 500 MHz) δ 7.71 (d, J=2.4 Hz, 1H), 7.48-7.42 (m, 2H), 7.37-7.26 (m, 4H), 2.40 (s, 1H), 1.74 (s, 3H), 1.48 (s, 9H). MS (ESI) 470 [M+H]$^+$.

Example 9

Preparation of 2-chloro-N-(cyclopropylmethyl)-N-[4-(1,1,1-trifluoro-2-hydroxypropan-2-yl)phenyl]benzenesulfonamide (9)

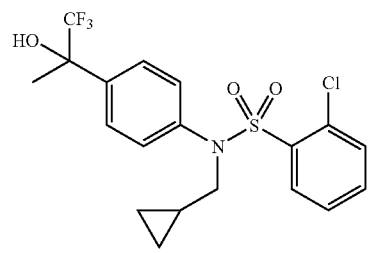

9

Following steps (a) and (b) described above in Example 7, but substituting 2-chlorobenzenesulfonyl chloride for 2,5-dichlorobenzenesulfonyl chloride in step (a) and (bromomethyl)cyclopropane for isopropyl iodide in step (b), 2-chloro-N-(cyclopropylmethyl)-N-[4-(1,1,1-trifluoro-2-hydroxypropan-2-yl)phenyl]benzenesulfonamide (9) was prepared. $^1$H NMR ($CDCl_3$, 500 MHz) δ 7.83 (dd, J=1.6, 8.0 Hz, 1H), 7.54-7.40 (m, 4H), 7.29-7.26 (m, 2H), 7.24-7.21 (m, 1H), 3.71 (d, J=7.1 Hz, 2H), 2.35 (s, 1H), 1.74 (s, 3H), 1.02-0.90 (m, 1H), 0.48-0.43 (m, 2H), 0.18-0.13 (m, 2H). MS (ESI) 434 [M+H]$^+$.

Example 10

Preparation of 2,5-dichloro-N-isobutyl-N-[4-(1,1,1-trifluoro-2-hydroxypropan-2-yl)phenyl]benzenesulfonamide (10)

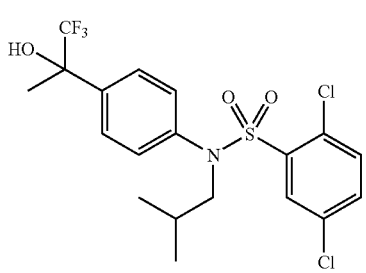

10

Following step (b) described above in Example 7, but substituting 1-bromo-2-methylpropane for isopropyl iodide, 2,5-dichloro-N-isobutyl-N-[4-(1,1,1-trifluoro-2-hydroxypropan-2-yl)phenyl]benzenesulfonamide (10) was prepared. ¹H NMR (CDCl₃, 400 MHz) δ 7.78 (d, J=2.3 Hz, 1H), 7.50 (d, J=8.6 Hz, 2H), 7.39-7.37 (m, 2H), 7.26 (d, J=8.6 Hz, 2H), 3.66 (d, J=7.4 Hz, 2H), 2.33 (s, 1H), 1.75 (s, 3H), 1.70-1.62 (m, 1H), 0.95 (d, J=6.6 Hz, 3H), 0.95 (d, J=6.6 Hz, 3H). MS (ESI) 470 [M+H]⁺.

Example 11

Preparation of 2-chloro-N-isopropyl-5-nitro-N-[4-(1,1,1-trifluoro-2-hydroxypropan-2-yl)phenyl]benzenesulfonamide (11)

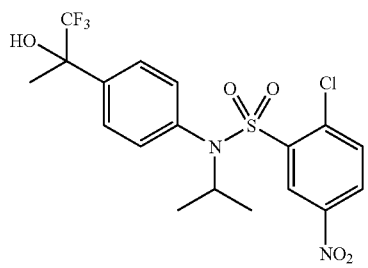

11

Following steps (a) and (b) described above in Example 7, but substituting 2-chloro-5-nitrobenzenesulfonyl chloride for 2,5-dichlorobenzenesulfonyl chloride in step (a), 2-chloro-N-isopropyl-5-nitro-N-[4-(1,1,1-trifluoro-2-hydroxypropan-2-yl)phenyl]benzenesulfonamide (11) was prepared. ¹H NMR (CDCl₃, 400 MHz) δ 8.66 (d, J=2.7 Hz, 1H), 8.29 (dd, J=2.7, 8.7 Hz, 1H), 7.73 (d, J=8.7 Hz, 1H), 7.53 (d, J=8.4 Hz, 2H), 7.10 (d, J=8.4 Hz, 2H), 4.80-4.73 (m, 1H), 2.35 (s, 1H), 1.77 (s, 3H), 1.19 (d, J=6.4 Hz, 3H), 1.18 (d, J=6.4 Hz, 3H). MS (ESI) 467 [M+H]⁺.

Example 12

Preparation of 5-amino-2-chloro-N-isopropyl-N-[4-(1,1,1-trifluoro-2-hydroxypropan-2-yl)phenyl]benzenesulfonamide (12)

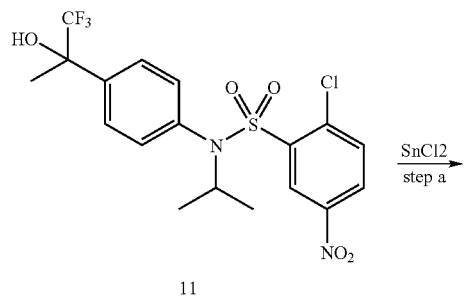

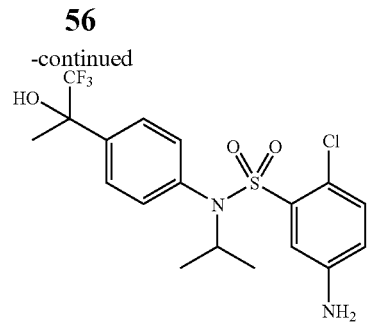

12

A solution of 2-chloro-N-isopropyl-5-nitro-N-[4-(1,1,1-trifluoro-2-hydroxypropan-2-yl)phenyl]benzenesulfonamide (11) (704 mg, 1.50 mmol, 1.0 equiv) in EtOH (40 mL) was treated with SnCl₂·2H₂O (1.70 g, 7.50 mmol, 5.0 equiv). After stirring at 75° C. for 2 h, the reaction mixture was concentrated under reduced pressure, diluted (EtOAc) and washed (3×1 M aqueous NaOH and 1×brine). The organics were dried (Na₂SO₄) and concentrated under reduced pressure. Flash chromatography of the residue (SiO₂, 30-40% EtOAc/Hexane, gradient elution) gave the product as a white foam. ¹H NMR (DMSO-d₆, 500 MHz) δ 7.59 (d, J=8.6 Hz, 2H), 7.28 (d, J=8.6 Hz, 1H), 7.12 (d, J=8.6 Hz, 2H), 7.08 (d, J=2.8 Hz, 1H), 6.73 (dd, J=2.8, 8.6 Hz, 1H), 6.65 (s, 1H), 5.67 (s, 1H), 4.50-4.42 (m, 1H), 1.67 (s, 3H), 1.04 (d, J=6.6 Hz, 3H), 1.03 (d, J=6.6 Hz, 3H). MS (ESI) 437 [M+H]⁺.

Example 13

Preparation of 5-bromo-2-chloro-N-isopropyl-N-[4-(1,1,1-trifluoro-2-hydroxypropan-2-yl)phenyl]benzenesulfonamide (13)

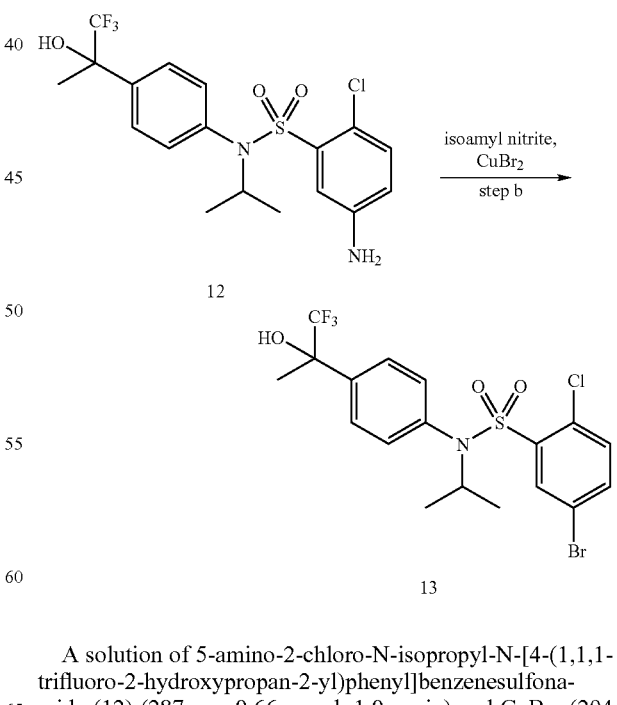

A solution of 5-amino-2-chloro-N-isopropyl-N-[4-(1,1,1-trifluoro-2-hydroxypropan-2-yl)phenyl]benzenesulfonamide (12) (287 mg, 0.66 mmol, 1.0 equiv) and CuBr₂ (294 mg, 1.32 mmol, 2.0 equiv) in CH₃CN (6.0 mL) was treated with isoamyl nitrite (180 μL, 1.32 mmol, 2.0 equiv) at 0° C.

After stirring at 25° C. for 1 h, the solution was diluted (EtOAc) and washed (3×brine). The organics were dried (Na$_2$SO$_4$) and concentrated under reduced pressure. Flash chromatography of the residue (SiO$_2$, 20% EtOAc/Hexane) gave the product as a white solid. $^1$H NMR (CDCl$_3$, 500 MHz) δ 7.96 (d, J=2.3 Hz, 1H), 7.57 (dd, J=2.3, 8.5 Hz, 1H), 7.53 (d, J=8.5 Hz, 2H), 7.39 (d, J=8.5 Hz, 1H), 7.12 (d, J=8.5 Hz, 2H), 4.79-4.70 (m, 1H), 2.37 (s, 1H), 1.77 (s, 3H), 1.16 (d, J=6.7 Hz, 3H), 1.15 (d, J=6.7 Hz, 3H). MS (ESI) 500 [M+H]$^+$.

Example 14

Preparation of 2-chloro-N-ethyl-N-[4-(1,1,1-trifluoro-2-hydroxypropan-2-yl)phenyl]benzenesulfonamide (14)

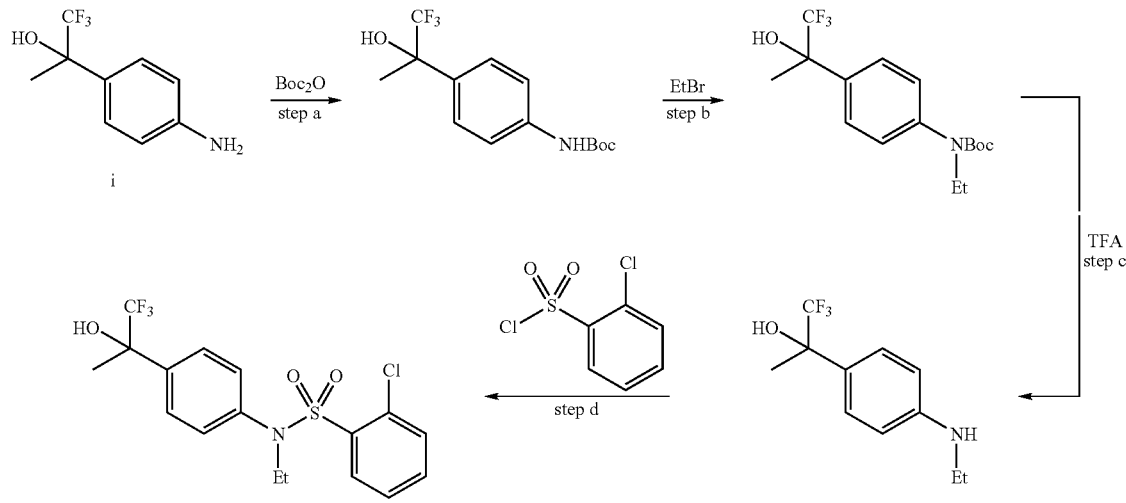

(a) tert-Butyl 4-(1,1,1-trifluoro-2-hydroxypropan-2-yl)phenylcarbamate. A solution of 2-(4-aminophenyl)-1,1,1-trifluoropropan-2-ol (i) prepared above in step (b) in Example 1 (13.8 g, 67.3 mmol, 1.0 equiv) in THF (100 mL) was treated with NaOH (33.5 mL, 2.0 M in H$_2$O, 1.0 equiv) and Boc$_2$O (14.6 g, 67.3 mmol, 1.0 equiv) at 0° C. and heated to 40° C. After stirring for 12 h, the reaction was cooled to 25° C., diluted (saturated aqueous NaHCO$_3$), extracted (3×EtOAc) and washed (1×brine). The organics were dried (MgSO$_4$) and concentrated under reduced pressure. Flash chromatography of the residue (SiO$_2$, 5% MeOH/CH$_2$Cl$_2$) gave the product as a white solid.

(b) tert-Butyl ethyl[4-(1,1,1-trifluoro-2-hydroxypropan-2-yl)phenyl]carbamate. A solution of tert-butyl 4-(1,1,1-trifluoro-2-hydroxypropan-2-yl)phenylcarbamate prepared above in step (a) (500 mg, 1.64 mmol, 1.0 equiv) in DMF (5.0 mL) was treated at 0° C. with NaH (138 mg, 60% in mineral oil, 3.44 mmol, 2.1 equiv). The reaction was stirred for 20 min at 0° C. and ethyl bromide (138 µL, 1.80 mmol, 1.1 equiv) was added. After stirring for 50 min at 25° C., the reaction was diluted (EtOAc), washed (3×brine), dried (Na$_2$SO$_4$), and concentrated under reduced pressure. Flash chromatography of the residue (SiO$_2$, 15% EtOAc/Hexane) provided the product as a pale yellow foam.

(c) 2-(4-(Ethylamino)phenyl)-1,1,1-trifluoropropan-2-ol. A sample of tert-butyl ethyl[4-(1,1,1-trifluoro-2-hydroxypropan-2-yl)phenyl]carbamate prepared above in step (b) (182 mg, 0.55 mmol, 1.0 equiv) was treated with trifluoroacetic acid (2.1 mL, 27.5 mmol, 50 equiv) and the mixture was stirred at 25° C. for 20 min. The volatiles were removed under a stream of N$_2$ and the residue was diluted (EtOAc) and washed (1×saturated aqueous NaHCO$_3$ and 1×brine). The organics were dried (Na$_2$SO$_4$) and concentrated under reduced pressure to provide the product as a yellow solid.

(d) 2-Chloro-N-ethyl-N-[4-(1,1,1-trifluoro-2-hydroxypropan-2-yl)phenyl]benzenesulfonamide (14). A solution of 2-(4-(ethylamino)phenyl)-1,1,1-trifluoropropan-2-ol prepared above in step (c) (40 mg, 0.17 mmol, 1.0 equiv) and 2-chlorobenzenesulfonyl chloride (37 mg, 0.17 mmol, 1.0 equiv) in CH$_2$Cl$_2$ (1.0 mL) was treated with pyridine (42 µL, 0.51 mmol, 3.0 equiv). After stirring at 25° C. for 12 h, the solution was diluted (EtOAc) and washed (1×1 N aqueous HCl, 1×saturated aqueous NaHCO$_3$, and 1×brine). The organics were dried (Na$_2$SO$_4$) and concentrated under reduced pressure. Flash chromatography of the residue (SiO$_2$, 20% EtOAc/Hexane) gave the product as a white solid. $^1$H NMR (CDCl$_3$, 500 MHz) δ 7.83 (dd, J=1.5, 7.9 Hz, 1H), 7.52-7.47 (m, 3H), 7.45-7.42 (m, 1H), 7.27-7.25 (m, 1H), 7.24-7.21 (m, 2H), 3.88 (q, J=7.1 Hz, 2H), 2.36 (s, 1H), 1.74 (s, 3H), 1.15 (t, J=7.1 Hz, 3H). MS (ESI) 408 [M+H]$^+$.

Example 15

Preparation of 2-chloro-N-methyl-N-[4-(1,1,1-trifluoro-2-hydroxypropan-2-yl)phenyl]benzenesulfonamide (15)

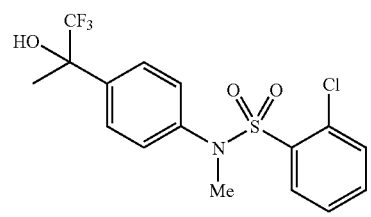

Following steps (b), (c), and (d) described above in Example 14, but substituting methyl iodide for ethyl bromide in step (b), 2-chloro-N-methyl-N-[4-(1,1,1-trifluoro-2-hydroxypropan-2-yl)phenyl]benzenesulfonamide (15) was prepared. $^1$H NMR (CDCl$_3$, 400 MHz) δ 7.91 (dd, J=1.5, 8.3 Hz, 1H), 7.54-7.43 (m, 4H), 7.34-7.29 (m, 1H), 7.24-7.21 (m, 2H), 3.41 (s, 3H), 2.32 (s, 1H), 1.75 (s, 3H). MS (ESI) 394 [M+H]$^+$.

Example 16

Preparation of 2-chloro-N-(2-chloro-4-(1,1,1-trifluoro-2-hydroxypropan-2-yl)phenyl)-N-isopropylbenzenesulfonamide (16)

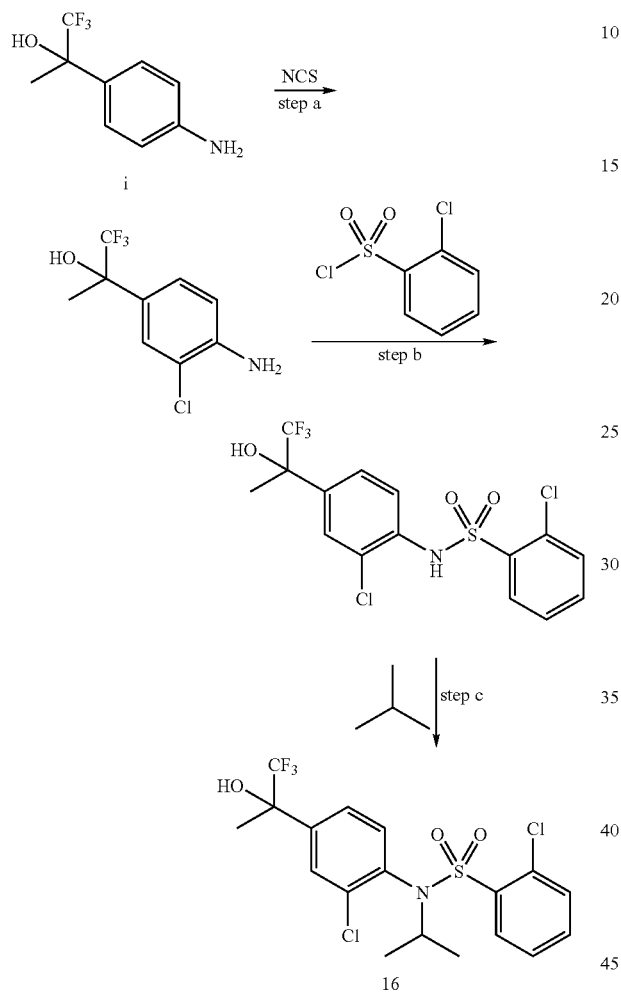

(a) 2-(4-Amino-3-chlorophenyl)-1,1,1-trifluoropropan-2-ol. A 100 mL flask was charged with 410 mg 2-(4-aminophenyl)-1,1,1-trifluoropropan-2-ol (i) (2.0 mmol, 1.0 equiv), 267 mg N-chlorosuccinimide (2.0 mmol, 1.0 equiv) and 3 mL acetonitrile. The flask was equipped with a reflux condenser, and placed into a preheated 85° C. bath with stirring for 3 h. The solution was diluted with H$_2$O, extracted (10% MeOH/CH$_2$Cl$_2$), washed (brine), dried (Na$_2$SO$_4$) and concentrated under reduced pressure. Flash chromatography of the residue (SiO$_2$, 5% MeOH/CH$_2$Cl$_2$) provided the product as a white solid.

(b) 2-Chloro-N-(2-chloro-4-(1,1,1-trifluoro-2-hydroxypropan-2-yl)phenyl)benzenesulfonamide. 2-(4-Amino-3-chlorophenyl)-1,1,1-trifluoropropan-2-ol (95.6 mg, 0.4 mmol, 1.0 equiv) was combined in a flask with 84.4 mg 2-chlorosulfonyl chloride (0.4 mmol, 1.0 equiv), 0.5 mL pyridine and 0.5 mL acetone, and the reaction mixture was refluxed for 4 h. The solution was cooled, diluted with H$_2$O, extracted (EtOAc), washed (brine), dried (Na$_2$SO$_4$) and concentrated under reduced pressure. Flash chromatography of the residue (SiO$_2$, 2% MeOH/CH$_2$Cl$_2$) gave the product as a white solid.

(c) 2-Chloro-N-(2-chloro-4-(1,1,1-trifluoro-2-hydroxypropan-2-yl)phenyl)-N-isopropylbenzenesulfonamide (16). To a suspension of 15 mg 2-chloro-N-(2-chloro-4-(1,1,1,-trifluoro-2-hydroxypropan-2-yl)phenyl)benzenesulfonamide (0.036 mmol, 1.0 equiv), 40 mg K$_2$CO$_3$ (0.29 mmol, 8.0 equiv) and 0.5 mL DMF was added 123 mg isopropyl iodide (0.73 mmol, 20.0 equiv). The resulting suspension was heated to 120° C. with stirring for 1 h, the suspension was diluted with sat. NaHCO$_3$, extracted (CH$_2$Cl$_2$), washed (brine), dried (Na$_2$SO$_4$) and concentrated under reduced pressure. Flash chromatography of the residue (SiO$_2$, 1% MeOH/CH$_2$Cl$_2$) gave the product (16) as a white solid. $^1$HNMR (CDCl$_3$, 500 MHz) δ 7.84 (dd, J=8.0, 1.5 Hz, 1 H), 7.66 (s, 0.5 H), 7.60 (s, 0.5 H), 7.56-7.48 (m, 3 H), 7.42 (dd, J=7.5, 3.5 Hz, 1 H), 7.29 (dd, J=7.5, 7.5 Hz, 1 H), 4.9 (m, 1 H), 2.46 (s, 1 H), 1.78 (s, 3 H), 1.27 (dd, J=5.0, 5.0 Hz, 3H), 1.18 (dd, J=7.5, 7.5 Hz, 3 H). MS (ESI) 456.0 (M+H$^+$).

Example 17

Synthesis of 2-chloro-N-(2-chloro-4-(1,1,1-trifluoro-2-hydroxypropan-2-yl)phenyl)-N-ethylbenzenesulfonamide (17)

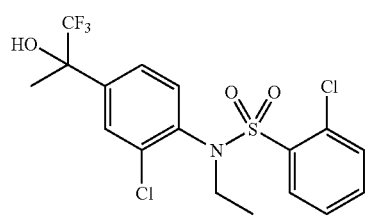

Using the methods described in Example 16 above, substituting ethyl bromide for isopropyl iodide, 2-chloro-N-(2-chloro-4-(1,1,1-trifluoro-2-hydroxypropan-2-yl)phenyl)-N-ethylbenzenesulfonamide (17) was prepared. $^1$H NMR (CDCl$_3$, 500 MHz) δ 7.82 (dd, J=8.0, 1.5 Hz, 1 H), 7.61 (s, 1 H), 7.53 (d, J=7.5 Hz, 1 H), 7.48-7.45 (m, 2 H), 7.41 (d, J=8.5 1 H), 7.28 (dd, J=8.5, 8.5 Hz, 1 H), 4.0 (m, 2 H), 2.80 (s, 1 H), 1.78 (s, 3 H), 1.19 (dd, J=7.5, 7.5 Hz, 3 H). MS (ESI) 442.0 (M+H$^+$).

Example 18

Synthesis of 2-chloro-N-(1-fluoropropan-2-yl)-N-(4-(1,1,1-trifluoro-2-hydroxypropan-2-yl)phenyl)benzenesulfonamide (18)

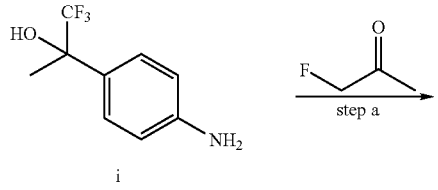

-continued

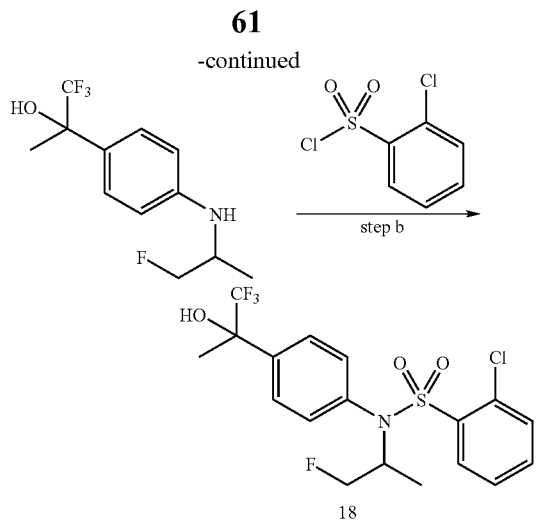

(a) 1,1,1-Trifluoro-2-(4-(1-fluoropropan-2-ylamino)phenyl)propan-2-ol. To a 100 mL flask charged with 820 mg 2-(4-aminophenyl)-1,1,1-trifluoropropan-2-ol (i) (4.0 mmol, 1.0 equiv), 1.44 mL AcOH and 20 mL acetonitrile were added 1.52 g fluoroacetone (20.0 mmol, 5.0 equiv) and 1.24 g NaCNBH₃ (20.0 mmol, 5 equiv). After stirring for 2 h at room temperature, the solution was diluted with 1 N NaOH, extracted (EtOAc), washed (brine), dried (Na₂SO₄) and concentrated under reduced pressure. Flash chromatography of the residue (SiO₂, CH₂Cl₂) provided the product as a white solid.

(b) 2-Chloro-N-(1-fluoropropan-2-yl)-N-(4-(1,1,1-trifluoro-2-hydroxypropan-2-yl)phenyl)benzenesulfonamide (18). 1,1,1-Trifluoro-2-(4-(1-fluoropropan-2-ylamino)phenyl)propan-2-ol (53 mg, 0.2 mmol, 1.0 equiv) was combined in a flask with 126.7 mg 2-chlorosulfonyl chloride (0.6 mmol, 3.0 equiv) and 1.0 mL pyridine, and the reaction mixture was refluxed for 2 h. The solution was diluted with H₂O, extracted (EtOAc), washed (brine), dried (Na₂SO₄) and concentrated under reduced pressure. Flash chromatography of the residue (SiO₂, 30% EtOAc/Hexane) gave the product (18) as a light yellow solid. ¹HNMR (CDCl₃, 500 MHz) δ 7.82 (dd, J=8.0, 1.5 Hz, 1 H), 7.56 (d, J=8.0 Hz 1H), 7.53 (d, J=7.5 Hz, 2 H), 7.48 (ddd, J=8.5, 8.5, 1.5 Hz, 1 H), 7.28 (dd, J=8.5, 8.5 Hz, 1 H), 7.16 (dd, J=8.5, 1.5 Hz, 2 H), 4.9 (m, 1 H), 4.34-4.13 (m, 2 H), 2.49 (s, 1 H), 1.77 (s, 3 H), 1.16 (d, J=8.5 Hz, 3 H). MS (ESI) 440.2 (M+H⁺).

Example 19

Preparation of 2,5-dichloro-N-(2,2,2-trifluoroethyl)-N-[4-(1,1,1-trifluoro-2-hydroxypropan-2-yl)phenyl]benzenesulfonamide (19)

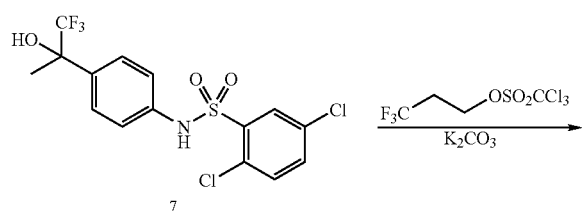

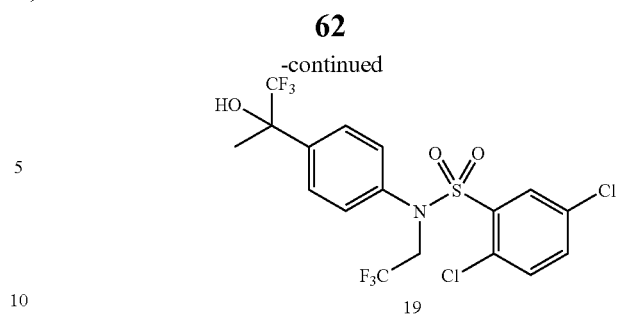

A mixture of 2,5-dichloro-N-(4-(1,1,1-trifluoro-2-hydroxypropan-2-yl)phenyl)benzenesulfonamide (7) (prepared as in Example 7, 60.0 mg, 0.146 mmol), K₂CO₃ (161.5 mg, 1.17 mmol) and CF₃CH₂OSO₂CCl₃ (204 mg, 0.723 mmol) in DMF (1.0 mL) was stirred at 110° C. for 18 h. The reaction mixture was cooled to room temperature, diluted with Et₂O (10 mL). The solution was washed with water and brine, dried, and concentrated. Flash chromatography of the residue, using 3:7 EtOAc-Hexane, gave 2,5-dichloro-N-(4-(1,1,1-trifluoro-2-hydroxypropan-2-yl)phenyl)-N-(2,2,2-trifluoroethyl)benzenesulfonamide (19). ¹H NMR (CDCl₃) δ 7.73 (s, 1H), 7.51(d, J=8.0 Hz, 2 H), 7.45(d, J=8.4 Hz, 1 H), 7.41(d, J=8.4 Hz, 1 H), δ 7.27(d, J=8.0 Hz, 2 H), 4.48(m, 2 H), 2.50(s, 1H), 1.73(s, 3 H). MS (ESI) 496.3 (M+H⁺).

Example 20

Preparation of 2,3-dichloro-N-(2,2,2-trifluoroethyl)-N-[4-(1,1,1-trifluoro-2-hydroxypropan-2-yl)phenyl]benzenesulfonamide (20)

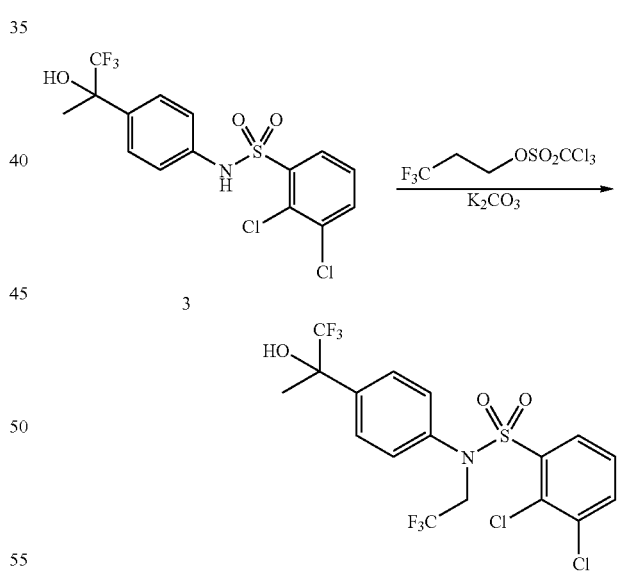

A mixture of 2,3-dichloro-N-(4-(1,1,1-trifluoro-2-hydroxypropan-2-yl)phenyl)benzenesulfonamide (3) (prepared as in Example 6, 32.0 mg, 0.077 mmol), K₂CO₃ (86 mg, 0.62 mmol) and CF₃CH₂OSO₂ CCl₃ (109 mg, 0.385 mmol) in DMF (1.0 mL) was stirred at 110° C. for 18 h. The reaction mixture was cooled to room temperature, diluted with Et₂O (10 mL). The solution was washed with water and brine, dried, and concentrated. Flash chromatography of the residue, using 3:7 EtOAc-Hexane, gave 2,3-dichloro-N-(4-(1,1, 1-trifluoro-2-hydroxypropan-2-yl)phenyl)-N-(2,2,2-trifluoroethyl)benzenesulfonamide (20). $^1$H NMR (CDCl$_3$) δ 7.70 (dd, J=8.0, 1.6 Hz, 1 H), 7.61(dd, J=8.0, 1.6 Hz, 1 H), 7.48(d, J=8.0 Hz, 2H), 7.27(d, J=8.0 Hz, 2 H), δ 7.15(dd, J=8.0, 8.0 Hz, 1 H), 4.52(m, 2 H), 2.43(br, 1H), 1.72(s, 3 H). MS (ESI) 496.2 (M+H$^+$).

Example 21

Preparation of 2-chloro-N-(2,2,2-trifluoroethyl)-N-[4-(1,1,1-trifluoro-2-hydroxypropan-2-yl)phenyl]benzenesulfonamide (21)

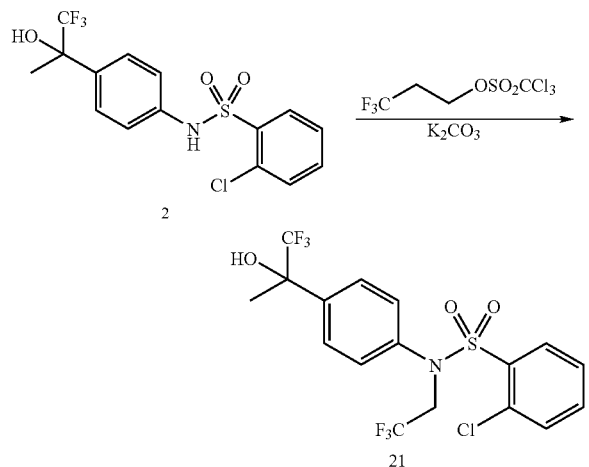

A mixture of 2-chloro-N-(4-(1,1,1-trifluoro-2-hydroxypropan-2-yl)phenyl)benzenesulfonamide (2) (prepared as in Example 7, 48.4 mg, 0.128 mmol), K$_2$CO$_3$ (141.3 mg, 1.02 mmol) and CF$_3$CH$_2$OSO$_2$CCl$_3$ (181 mg, 0.64 mmol) in DMF (1.0 mL) was stirred at 110° C. for 18 h. The reaction mixture was cooled to room temperature, diluted with Et$_2$O (10 mL). The solution was washed with water and brine, dried, and concentrated. Flash chromatography of the residue, using 3:7 EtOAc-hexane, gave 2-chloro-N-(4-(1,1,1-trifluoro-2-hydroxypropan-2-yl)phenyl)-N-(2,2,2-trifluoroethyl)benzenesulfonamide 21. $^1$H NMR (CDCl$_3$) δ 7.77(dd, J=8.0, 1.0 Hz, 1H), 7.54(d, J=8.0 Hz, 1 H), 7.52-7.43(m, 3 H), 7.29(d, J=8.0, 2 H), δ 7.23(dd, J=8.0, 8.0 Hz, 1 H), 4.55(m, 2 H), 2.57(br, 1H), 1.74(s, 3 H). MS (ESI) 462.2 (M+H$^+$).

Example 22

Preparation of 2,3-dichloro-N-cyclopropyl-N-[4-(1,1,1-trifluoro-2-hydroxypropan-2-yl)phenyl]benzenesulfonamide (22)

(a) Preparation of an aryl halide intermediate. To 4'-bromoacetophenone (10 g, 50 mmol) in THF (80 mL) cooled to 0° C. was added TMSCF$_3$ (11 mL, 75 mmol). Over a period of 5 min, 1 M TBAF in THF (0.38 mL) was added drop wise to the solution. After 30 min., the cooling source was removed and the solution was stirred for 2.5 h. The solvent was removed by rotary evaporation. The residue was dissolved in CH$_2$Cl$_2$ (200 mL) and extracted against water (200 mL). The partitioned organics were dried with Na$_2$SO$_4$. Following removal of the CH$_2$Cl$_2$ by rotary evaporation, the residue was distilled (78-82° C., 0.1 mm Hg) to yield the bromide.

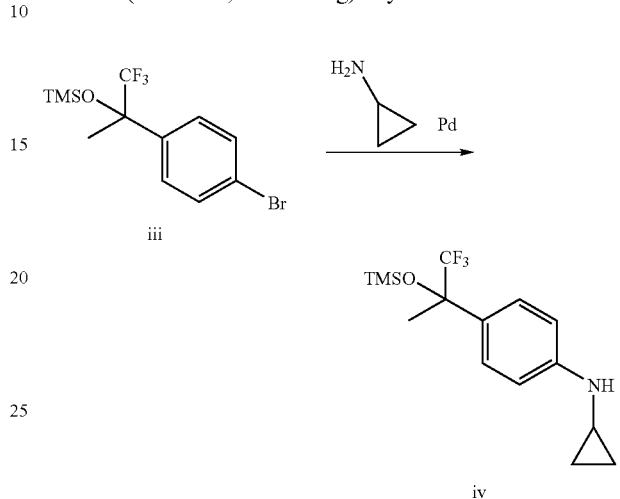

(b) General procedure for Pd catalyzed amination of aryl halides. To an argon purged sealed tube containing Pd$_2$(dba)$_3$ (0.27 g, 0.30 mmol), (±)-BINAP (0.56 g, 0.90 mmol), and NaOtBu (1.4 g, 14 mmol) was added degassed toluene (10 mL). Cyclopropylamine (0.84 mL, 12 mmol), bromide iii (prepared as above, 4.4 g, 10 mmol), and toluene (10 mL) were combined under argon in a separate vial and added to the catalyst suspension under argon. The tube was sealed under argon and heated in an 80° C. oil bath for 16 h. The cooled reaction suspension was diluted with CH$_2$Cl$_2$ (200 mL) and extracted against water (100 mL). The organics were dried with Na$_2$SO$_4$ and removed in vacuo. Silica gel column chromatography (elution with 5% ethyl acetate in hexanes) afforded alkyl aniline iv.

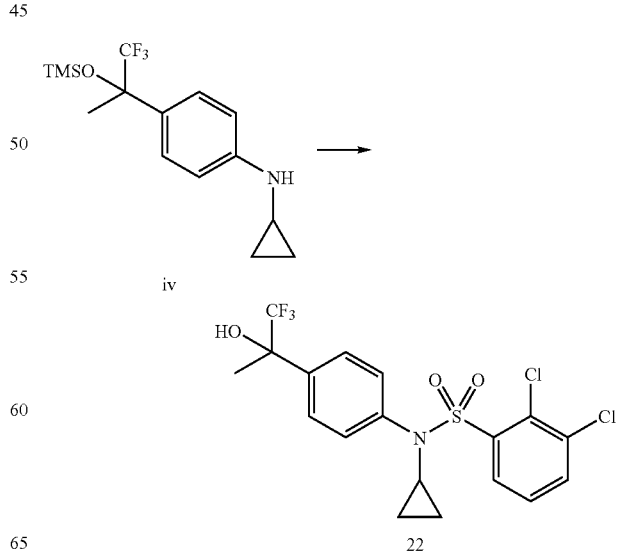

(c) 2,3-Dichloro-N-cyclopropyl-N-[4-(1,1,1-trifluoro-2-hydroxypropan-2-yl)phenyl]benzenesulfonamide (22). To cyclopropyl aniline iv prepared above (0.10 g, 0.32 mmol) and 2,3-dichlorobenzenesulfonyl chloride (0.093 g, 0.38 mmol) was added pyridine (0.5 mL). The solution was heated to 100° C. for a period of 30 min, diluted with H$_2$O (5 mL) and acidified (pH 1) with 1 M HCl. Following extraction of the resulting mixture with CH$_2$Cl$_2$ (2×1 mL), the collected organics were added to 1 M TBAF in THF (2 mL) and the resulting solution was extracted with H$_2$O (2 mL). Partitioned organics were dried with Na$_2$SO$_4$, and concentrated in vacuo. Silica-gel column chromatography (eluting with 15% ethyl acetate in hexanes) afforded 22. $^1$H NMR (400 MHz, CDCl$_3$): δ 0.70-0.90 (m, 4H), 1.79 (s, 3H), 2.37 (bs, 1H), 2.9-3.0 (m, 1H), 7.29 (m 1 H), 7.31 (d, J=9 Hz, 2H), 7.53 (d, J=9 Hz, 2H), 7.68 (d, J=8 Hz, 1H), 7.96 (d, J=8 Hz, 1H).

Example 23

Preparation of 2,5-dichloro-N-cyclobutyl-N-[4-(1,1,1-trifluoro-2-hydroxypropan-2-yl)phenyl]benzenesulfonamide (23)

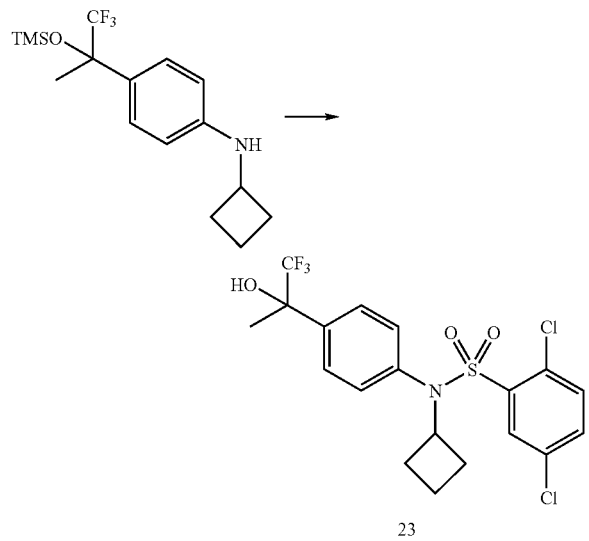

To a solution of the cyclobutyl aniline prepared according to the general procedure for the preparation of cyclopropyl aniline iv (0.082 mg, 0.25 mmol) in CHCl$_3$ (0.25 mL) was added pyridine (0.040 mL, 0.50 mmol) followed by the portion wise addition of 2,5-dichlorobenzenesulfonyl chloride (0.073 mg, 0.30 mmol). The reaction was stirred at room temperature for 20 h. To the reaction was added a solution of 1 M TBAF in THF (0.25 mL). The organics were washed with 2.5 M HCl (0.5 mL), dried with Na$_2$SO$_4$, and concentrated in vacuo. Silica gel column chromatography (gradient of 10 to 30% ethyl acetate in hexanes) afforded 23. $^1$H NMR (400 MHz, CDCl$_3$): δ 1.45-1.65 (m, 2H), 1.79 (s, 3H), 1.85-1.95 (m, 2 H), 2.15-2.25 (m, 2H), 2.45 (s, 1H), 4.87-4.95 (m, 1H), 7.08 (d, J=8.8 Hz, 2 H), 7.4-7.5 (m, 2 H), 7.56 (d, J=8.4 Hz, 2 H), 7.78 (s, 1H).

Example 24

Preparation of 2,5-dichloro-N-phenyl-N-[4-(1,1,1-trifluoro-2-hydroxypropan-2-yl)phenyl]benzenesulfonamide (24)

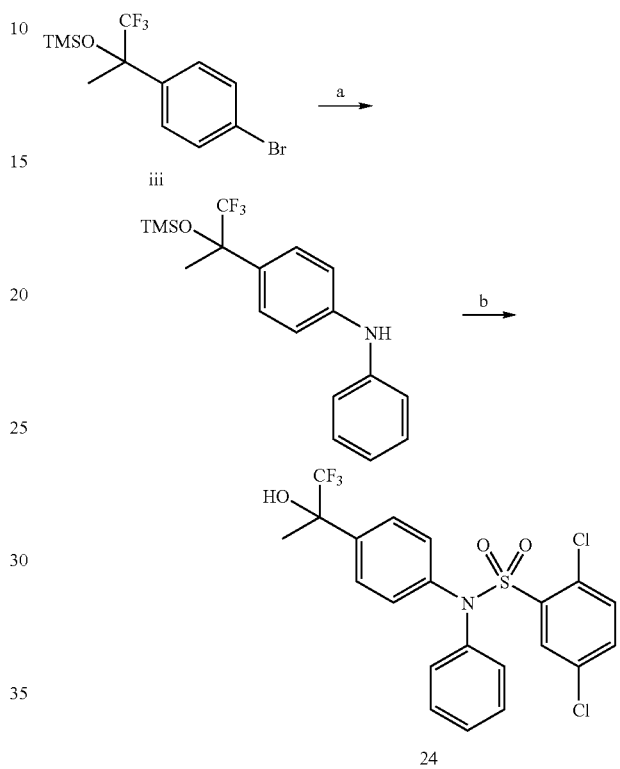

(a) To an argon purged tube sealed with a rubber septum and containing Pd$_2$(dba)$_3$ (0.055 g, 0.060 mmol) and (±)-BINAP (0.110 g, 0.18 mmol) was added toluene (2 mL). The solution was stirred for 10 min. under argon at room temperature. To the solution was added the bromide prepared above (0.89 g, 2.0 mmol) and aniline (0.219 mL, 2.4 mmol). The seal was removed and Cs$_2$CO$_3$ (0.92 g, 2.8 mmol) was added followed by addition of toluene (2 mL). The tube was purged with argon and sealed with a Teflon stopper. The reaction mixture was heated to 100° C. for 20 h. After cooling, H$_2$O (5 mL) was added to the reaction, and the resulting suspension was extracted with ethyl acetate (2×5 mL). Combined organics were dried with MgSO$_4$, concentrated in vacuo, and purified by silica gel chromatography (eluting with 5% ethyl acetate in hexanes) to afford the diphenylaniline.

(b) 2,5-Dichloro-N-phenyl-N-[4-(1,1,1-trifluoro-2-hydroxypropan-2-yl)phenyl]benzenesulfonamide (24). To the diphenylaniline prepared above (0.050 g, 0.141 mmol) in CHCl$_3$ (0.15 mL) and pyridine (0.023 mL, 0.28 mmol) was added portion wise 2,5-dichlorobenzenesulfonyl chloride. The reaction was stirred at room temperature for 5 h. To the reaction was added 1 M TBAF in THF (0.5 mL) followed by H$_2$O (2 mL). The suspension was extracted with CH$_2$Cl$_2$ (2×2 mL). The organics were dried with Na$_2$SO$_4$, concentrated in vacuo, and purified by silica gel chromatography (gradient 5-20% ethyl acetate in hexanes) to afford 24. $^1$H NMR (400

MHz, CDCl₃) δ 1.77 (s, 3H), 2.37 (s, 1H), 7.30-7.38 (m, 5 H), 7.42 (d, J=8.9 Hz, 2 H), 7.47-7.5 (m, 2H), 7.55 (d, J=9 Hz, 2 H), 7.93-7.97 (m, 1 H).

Example 25

Preparation of 2-cyclopropyl-N-isopropyl-N-[4-(1,1,1-trifluoro-2-hydroxypropan-2-yl)phenyl]benzenesulfonamide (25)

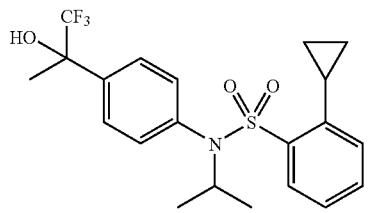

To a vessel containing 2-bromo-N-isopropyl-N-(4-(1,1,1-trifluoro-2-hydroxypropan-2-yl)phenyl)benzenesulfonamide (ii) (prepared as in Example 1, 0.020 g, 0.043 mmol), cyclopropylboronic acid (0.0070 g, 0.086 mmol), K₃PO₄ (0.018 g, 0.086 mmol), and Pd(PPh₃)₄ (0.0050 mg, 0.0043 mmol) under nitrogen atmosphere was added degassed toluene (0.40 mL) and H₂O (0.040 mL). The vessel was sealed under nitrogen atmosphere and heated in a 95° C. oil bath for 17.5 h. The reaction was cooled to room temperature, diluted with CH₂Cl₂ (2 mL), and extracted with H₂O (1 mL). The combined organics were dried with Na₂SO₄, concentrated in vacuo, and purified by silica gel chromatography (gradient elution 5-20% ethyl acetate in hexanes) to afford 25. ¹H NMR (400 MHz, CDCl₃) δ 0.85-0.090 (m, 2H), 1.10-1.19 (m, 8H), 1.78 (s, 3 H), 2.42 (bs, 1 H), 2.70-2.80 (m, 1 H), 4.53 (septet, J=6.7, 1H), 6.86 (d, J=7.8 Hz, 1H), 7.14 (t, J=7.3, 1H), 7.21 (d, J=8.6, 2H), 7.41 (t, J=7 Hz, 1 H), 7.53 (d, J=8.4 Hz, 2H), 7.84 (d, J=8 Hz, 1H).

Biological Examples

Procedures Useful for the Biological Evaluation of the Aniline Sulfonamide Derivatives In addition to the extensive literature disclosing the role of HSDs in various diseases and disorders, described herein are assays useful for testing the aniline sulfonamide derivatives of the present invention.

Assays

In vitro 11β-HSD1 (Hydroxysteroid Dehydrogenase 1) Activity Inhibitory Action

The 11β-HSD1 inhibitory activity was examined by quantitative determination by an SPA (scintillation proximity assay) system of the suppressive action on the conversion from cortisone to cortisol using human 11β-HSD1 (hereinafter recombinant 11β-HSD1) expressed using a baculo-virus system as an enzyme source. For the reaction, a reagent was added to a 96 well plate (96 well Opti-plates™-96 (Packard)) to the following final concentration and a volume of 100 μl was reacted at room temperature for 90 min. The reaction solution used was 0.1 μg/ml recombinant 11β-HSD1, 500 μM NADPH, 16 nM ³H cortisone (Amersham Biosciences, 1.78 Tbq/mol) dissolved in 0.1% BSA (Sigma)-containing PBS and the test drug was 2 μl of a compound solution (dissolved in DMSO). After 90 min, the reaction was stopped by adding PBS (40 μl, containing 0.1% BSA (Sigma)) containing 0.08 μg of anti-cortisol mouse monoclonal antibody (East Coast Biologics), 365 μg SPA PVT mouse antibody-binding beads (Amersham Biosciences) and 175 μM carbenoxolone (Sigma) to the reaction solution. After the completion of the reaction, the plate was incubated overnight at room temperature and the radioactivity was measured by Topcount (Packard). For control, the value (0% inhibition) of the well containing 2 μl of DMSO instead of the test drug was used, and for positive control, the value (100% inhibition) of the well containing carbenoxolone instead of the test drug at the final concentration of 50 μM was used. The inhibition (%) of the test drug was calculated by ((value of control−value of test drug)/(value of control−value of positive control))×100 (%). The IC₅₀ value was analyzed using a computer-based curve fitting soft.

This following example provides assays that are useful in evaluating and selecting a compound that modulates 11β-HSD1.

Biochemical 11β-HSD1 assay by SPA

Recombinant human, mouse and rat 11β-HSD1 were expressed in baculovirus expression system, isolated by affinity purification and used as the enzyme sources for cortisone to cortisol conversion in vitro. ³H-Cortisone (Amersham Bioscience, 1.78 Tbq/mol. 49 Ci/mmol) was used as the substrate, and a monoclonal anti-cortisol antibody and the scintillation proximity assay (SPA) system were used to detect the product of the 11β-HSD1-catalyzed reaction, ³H-cortisol. Reactions took place at room temperature for 90 min. in 96-well Opti-plates™-96 (Packard) in 100 μL volume with 2 μL test compounds or control in DMSO, 0.1 μg/mL 11β-HSD1 protein, 500 μM NADPH and 16 nM radioactive cortisone, in PBS buffer supplemented with 0.1% BSA (Sigma). Reaction was stopped with the addition of 40 μL buffer containing 0.08 μg anti-cortisol monoclonal antibody (East Coast Biologics), 365 μg SPA PVT antibody-binding beads (Amersham Biosciences) and 175 μM carbenoxolone (Sigma).

Plates were incubated at room temperature overnight before being read on a Topcount (Packard). The point of 50% inhibition of 11β-HSD1 enzyme activity (IC₅₀) was determined by computer-based curve fitting.

Cell-based 11β-HSD1 Assay by SPA

This cell-based assay measures the conversion of ³H-cortisone to ³H-cortisol in a HEK-293 cell line stably overexpressing human recombinant 11β-HSD1. HEK-293 cells were grown in DMEM/F12 supplemented with 10% fetal bovine serum, and plated onto poly-D-lysine-coated 96-well assay plates (Costar 3903), 100,000 cells per well in 50 μL assay media (phenol free DMEM/F12 (Invitrogen) +0.2% BSA+1% antibiotic-antimycotic solutions). The solution was incubated at 37° C. for 24 h, and the reaction was initiated by the addition of 25 μL of assay media containing compounds of desired concentration and 25 μL of assay media containing 40 nM of ³H-cortisone to each well. The reaction mixture was incubated at 37° C. for 90 min. and the reaction terminated by the addition of 25 μL of assay media containing 0.2 μg of anti-cortisol monoclonal antibody (East Coast Biologics), 500 μg SPA PVT antibody-binding beads (Amersham Biosciences) and 500 μM carbenoxolone (Sigma).

Plates were incubated at room temperature for at least 2 h before being read on Topcount (Packard). The point of 50% inhibition of 11β-HSD1 enzyme activity (IC₅₀) was determined by computer-based curve fitting.

The compounds prepared in the foregoing examples exhibited 11β-HSD1 enzyme activity (IC₅₀) in the assays ranging from <1 nM to 1000 nM.

We claim:
1. A compound having the formula (I):

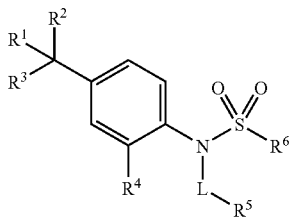

or a pharmaceutically acceptable salt or stereoisomer thereof, wherein:

$R^1$, $R^2$, and $R^3$, together with the carbon atom to which they are attached, are an (S)-trifluoromethyl carbinol group of the formula:

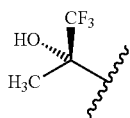

or an (R)-trifluoromethyl carbinol group of the formula:

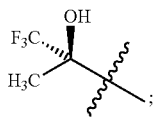

$R^4$ is a member selected from the group consisting of hydrogen, halogen, $(C_1-C_8)$alkyl and $(C_3-C_8)$cycloalkyl;

$R^5$ is selected from the group consisting of hydrogen, —OH, halogen, $(C_1-C_8)$alkyl, $(C_1-C_8)$haloalkyl, $(C_2-C_8)$heteroalkyl, $(C_3-C_8)$cycloalkyl, $(C_3-C_8)$heterocycloalkyl, C(O)R', C(O)NR'$_2$, NR'$_2$, NR'C(O)R', CN, NO$_2$, aryl, and heteroaryl;

$R^6$ is aryl or heteroaryl, or $R^6$ optionally may be combined with $R^5$ to form a 5- to 6-membered fused ring containing L, the nitrogen atom to which L is attached, and the sulfur atom to which $R^6$ is attached;

L is selected from the group consisting of a direct bond, $(C_1-C_4)$alkylene and $(C_2-C_4)$alkenylene;

wherein any cycloalkyl portion, heterocycloalkyl portion, aryl or heteroaryl portion is optionally substituted with from one to four members selected from the group consisting of halogen, —CN, —NO$_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $(C_2-C_8)$hydroxyalkyl, —C(O)R', —C(O)OR', —NR'C(O)OR", —OR', —SR', —OC(O)R', —C(O)N(R')$_2$, —S(O)R", —SO$_2$R", —SO$_2$N(R')$_2$, —N(R')$_2$ and —NR'C(O)R';

wherein each occurrence of R' is independently H or an unsubstituted member selected from the group consisting of $(C_1-C_8)$alkyl, $(C_2-C_8)$alkenyl, $(C_2-C_8)$alkynyl, $(C_1-C_4)$alkoxy$(C_1-C_4)$ alkyl, $(C_1-C_8)$haloalkyl, $(C_2-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$ alkyl, $(C_3-C_8)$ heterocycloalkyl$(C_1-C_6)$alkyl, heteroaryl $(C_1-C_6)$alkyl, and aryl$(C_1-C_6)$alkyl, wherein two R' groups, when attached to the same nitrogen atom, can be combined with the nitrogen atom to which they are attached to form a heterocycle or heteroaryl group; and wherein each occurrence of R" is independently an unsubstituted member selected from the group consisting of $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_2-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, heterocyclyl$(C_1-C_6)$alkyl, heteroaryl$(C_1-C_6)$alkyl and aryl$(C_1-C_6)$alkyl.

2. The compound according to claim 1, wherein L is a direct bond.

3. The compound according to claim 1, wherein $R^5$ is $(C_1-C_8)$alkyl.

4. The compound according to claim 3, wherein $R^5$ is $(C_1-C_3)$alkyl.

5. The compound according to claim 4, wherein $R^5$ is selected from the group consisting of methyl, ethyl, and isopropyl.

6. The compound according to claim 5, wherein $R^5$ is isopropyl.

7. The compound according to claim 1, wherein $R^5$ is $(C_3-C_8)$cycloalkyl.

8. The compound according to claim 7, wherein $R^5$ is cyclopropyl or cyclobutyl.

9. The compound according to claim 1, wherein $R^6$ is aryl.

10. The compound according to claim 9, wherein $R^6$ is aryl optionally substituted with one to four substituents.

11. The compound according to claim 10, wherein $R^6$ is dichloro-substituted phenyl.

12. The compound according to claim 10, wherein $R^6$ is 2-chloro-5-cyano-phenyl.

13. The compound according to claim 10, wherein $R^6$ is 2-chloro-phenyl.

14. The compound according to claim 10, wherein $R^6$ is 2-chloro-5-trifluoromethyl-phenyl.

15. The compound according to claim 1, wherein $R^5$ is selected from $(C_1-C_8)$alkyl and halo-$(C_1-C_8)$alkyl and $R^6$ is selected from phenyl and substituted phenyl.

16. The compound according to claim 15, wherein $R^5$ is selected from methyl, ethyl and isopropyl and $R^6$ is halosubstitued phenyl or CN-substituted phenyl.

17. The compound according to claim 1, wherein $R^5$ is a $C_3-C_8$ cycloalkyl moiety and $R^6$ is selected from phenyl and substituted phenyl.

18. The compound according to claim 17, wherein $R^5$ is cyclopropyl or cyclobutyl.

19. The compound according to claim 1, wherein $R^1$, $R^2$, and $R^3$, together with the carbon atom to which they are attached, are an (S)-trifluoromethyl carbinol group of the formula:

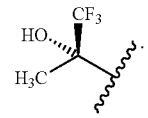

20. The compound according to claim 1, wherein $R^1$, $R^2$, and $R^3$, together with the carbon atom to which they are attached, are an (R)-trifluoromethyl carbinol group of the formula:

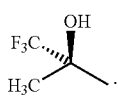

21. A pharmaceutical composition comprising a compound according to claim 1, and a pharmaceutically acceptable carrier.

22. A pharmaceutical composition comprising the compound according to claim 1, and an additional therapeutic agent.

23. A compound selected from the group consisting of:
N-isopropyl-N-[4-(1,1,1-trifluoro-2-hydroxypropan-2-yl) phenyl]benzenesulfonamide;
2-chloro-N-isopropyl-N-[4-(1,1,1-trifluoro-2-hydroxypropan-2-yl)phenyl]benzenesulfonamide;
2,3-dichloro-N-isopropyl-N-[4-(1,1,1-trifluoro-2-hydroxypropan-2-yl)phenyl]benzenesulfonamide;
2-fluoro-N-isopropyl-N-[4-(1,1,1-trifluoro-2-hydroxypropan-2-yl)phenyl]benzenesulfonamide;
2,6-dichloro-N-isopropyl-N-[4-(1,1,1-trifluoro-2-hydroxypropan-2-yl)phenyl]benzenesulfonamide;
2-chloro-4-cyano-N-isopropyl-N-[4-(1,1,1-trifluoro-2-hydroxypropan-2-yl)phenyl]benzenesulfonamide;
2,5-dichloro-N-isopropyl-N-[4-(1,1,1-trifluoro-2-hydroxypropan-2-yl)phenyl]benzenesulfonamide;
tert-butyl-2,5-dichloro-N-[4-(1,1,1-trifluoro-2-hydroxypropan-2-yl)phenyl]benzenesulfonamide;
2-chloro-N-(cyclopropylmethyl)-N-[4-(1,1,1-trifluoro-2-hydroxypropan-2-yl)phenyl]benzenesulfonamide;
2,5-dichloro-N-isobutyl-N-[4-(1,1,1-trifluoro-2-hydroxypropan-2-yl)phenyl]benzenesulfonamide;
2-chloro-N-isopropyl-5-nitro-N-[4-(1,1,1-trifluoro-2-hydroxypropan-2-yl)phenyl]benzenesulfonamide;
5-amino-2-chloro-N-isopropyl-N-[4-(1,1,1-trifluoro-2-hydroxypropan-2-yl)phenyl]benzenesulfonamide;
5-bromo-2-chloro-N-isopropyl-N-[4-(1,1,1-trifluoro-2-hydroxypropan-2-yl)phenyl]benzenesulfonamide;
2-chloro-N-ethyl-N-[4-(1,1,1-trifluoro-2-hydroxypropan-2-yl)phenyl]benzenesulfonamide;
2-chloro-N-methyl-N-[4-(1,1,1-trifluoro-2-hydroxypropan-2-yl)phenyl]benzenesulfonamide;
2-chloro-N-(2-chloro-4-(1,1,1-trifluoro-2-hydroxypropan-2-yl)phenyl)-N-isopropylbenzenesulfonamide;
2-chloro-N-(2-chloro-4-(1,1,1-trifluoro-2-hydroxypropan-2-yl)phenyl)-N-ethylbenzenesulfonamide;
2-chloro-N-(1-fluoropropan-2-yl)-N-(4-(1,1,1-trifluoro-2-hydroxypropan-2-yl)pheny)benzenesulfonamide;
2,5-dichloro-N-(2,2,2-trifluoroethyl)-N-[4-(1,1,1-trifluoro-2-hydroxypropan-2-yl)phenyl]benzenesulfonamide;
2,3-dichloro-N-(2,2,2-trifluoroethyl)-N-[4-(1,1,1-trifluoro-2-hydroxypropan-2-yl)phenyl]benzenesulfonamide;
2-chloro-N-(2,2,2-trifluoroethyl)-N-[4-(1,1,1-trifluoro-2-hydroxypropan-2-yl)phenyl]benzenesulfonamide;
2,3-dichloro-N-cyclopropyl-N-[4-(1,1,1-trifluoro-2-hydroxypropan-2-yl)phenyl]benzenesulfonamide;
2,5-dichloro-N-cyclobutyl-N-[4-(1,1,1-trifluoro-2-hydroxypropan-2-yl)phenyl]benzenesulfonamide;
2,5-dichloro-N-phenyl-N-[4-(1,1,1-trifluoro-2-hydroxypropan-2-yl)phenyl]benzenesulfonamide;
2-cyclopropyl-N-isopropyl-N-[4-(1,1,1-trifluoro-2-hydroxypropan-2-yl)phenyl]benzenesulfonamide, and
pharmaceutically acceptable salts, solvates, stereoisomers, and prodrugs thereof.

\* \* \* \* \*